(12) United States Patent
Landegren et al.

(10) Patent No.: US 10,612,093 B2
(45) Date of Patent: Apr. 7, 2020

(54) METHOD FOR SELECTING A TARGET NUCLEIC ACID SEQUENCE

(71) Applicant: Olink Bioscience AB, Uppsala (SE)

(72) Inventors: Ulf Landegren, Uppsala (SE); Rachel Yuan Nong, Uppsala (SE)

(73) Assignee: NAVINCI DIAGNOSTICS AB, Uppsala (SE)

( * ) Notice: Subject to any disclaimer, the term of this patent is extended or adjusted under 35 U.S.C. 154(b) by 0 days.

(21) Appl. No.: 15/500,407

(22) PCT Filed: Jul. 31, 2015

(86) PCT No.: PCT/EP2015/067723
§ 371 (c)(1),
(2) Date: Jan. 30, 2017

(87) PCT Pub. No.: WO2016/016450
PCT Pub. Date: Feb. 4, 2016

(65) Prior Publication Data
US 2019/0144940 A1 May 16, 2019

(30) Foreign Application Priority Data

Aug. 1, 2014 (GB) .................................. 1413717.8

(51) Int. Cl.
*C12Q 1/68* (2018.01)
*C07H 21/00* (2006.01)
*C12Q 1/6876* (2018.01)
*C12Q 1/6806* (2018.01)
*C12Q 1/6827* (2018.01)

(52) U.S. Cl.
CPC ......... *C12Q 1/6876* (2013.01); *C12Q 1/6806* (2013.01); *C12Q 1/6827* (2013.01)

(58) Field of Classification Search
CPC ................................. C12Q 1/68; C07H 21/00
See application file for complete search history.

(56) References Cited

U.S. PATENT DOCUMENTS

| 6,558,928 | B1 | 5/2003 | Landegren |
| 6,858,412 | B2 | 2/2005 | Willis et al. |
| 6,867,028 | B2 | 3/2005 | Janulaitis et al. |
| 7,883,849 | B1 | 2/2011 | Dahl |
| RE44,265 | E | 6/2013 | Landegren et al. |
| 8,518,640 | B2 | 8/2013 | Drmanac et al. |
| 2003/0022167 | A1 | 1/2003 | Alsmadi et al. |
| 2006/0166245 | A1 | 7/2006 | Potter et al. |
| 2007/0248965 | A1 | 10/2007 | Carstens et al. |
| 2009/0238896 | A1* | 9/2009 | Hernando ............ A61K 31/704 424/649 |
| 2013/0177915 | A1 | 7/2013 | Too et al. |
| 2013/0316917 | A1* | 11/2013 | Stemeers ............. C12Q 1/6806 506/2 |
| 2014/0134610 | A1* | 5/2014 | Pham .................. C12N 15/1072 435/6.1 |
| 2014/0170654 | A1 | 6/2014 | Landegren et al. |

FOREIGN PATENT DOCUMENTS

| WO | 03/012119 A2 | 2/2003 |
| WO | 03/044229 A1 | 5/2003 |
| WO | 2005/108608 A1 | 11/2005 |
| WO | 2007/018601 A1 | 2/2007 |
| WO | 2011/067378 A1 | 6/2011 |
| WO | 2011/161549 A3 | 12/2011 |
| WO | 2012/152942 A1 | 11/2012 |
| WO | 2014/076209 A1 | 5/2014 |
| WO | 2014/076214 A1 | 5/2014 |
| WO | 2015/071445 A1 | 5/2015 |

OTHER PUBLICATIONS

Hardenbol et al.,Multiplexed genotyping with sequence-tagged molecular inversion probes. Nature Biotechnology 21(5):673 (Year: 2003).*
Drmanac et al., Human Genome Sequencing Using Unchained Base Reads on Self-Assembling DNA Nanoarrays, Science, 327:78-81 (Jan. 1, 2010).
Fredriksson et al., Multiplex amplification of all coding sequences within 10 cancer genes by Gene-Collector, Nucleic Acids Research, 35(7):1-6 (published online Feb. 22, 2007).
DR. H. C. Kolb et al., Click Chemistry: Diverse Chemical Function from a Few Good Reactions, Angew. Chem. Int. Ed., 40:2004-2021 (2001).

* cited by examiner

*Primary Examiner* — Ethan C Whisenant
(74) *Attorney, Agent, or Firm* — Porter Wright Morris & Arthur LLP

(57) ABSTRACT

The present invention relates to a method of selecting a target region of interest (ROI) in a target nucleic acid molecule using a nucleic acid probe comprising sequences capable of directing the cleavage of a target nucleic acid molecule to release a fragment comprising the ROI and sequences capable of templating the circularisation and ligation of the target fragment. The circularised molecule thus obtained contains the selected ROI and may be subjected to further analysis and/or amplification etc. Also provided are probes and kits for use in such methods.

Figure 1:
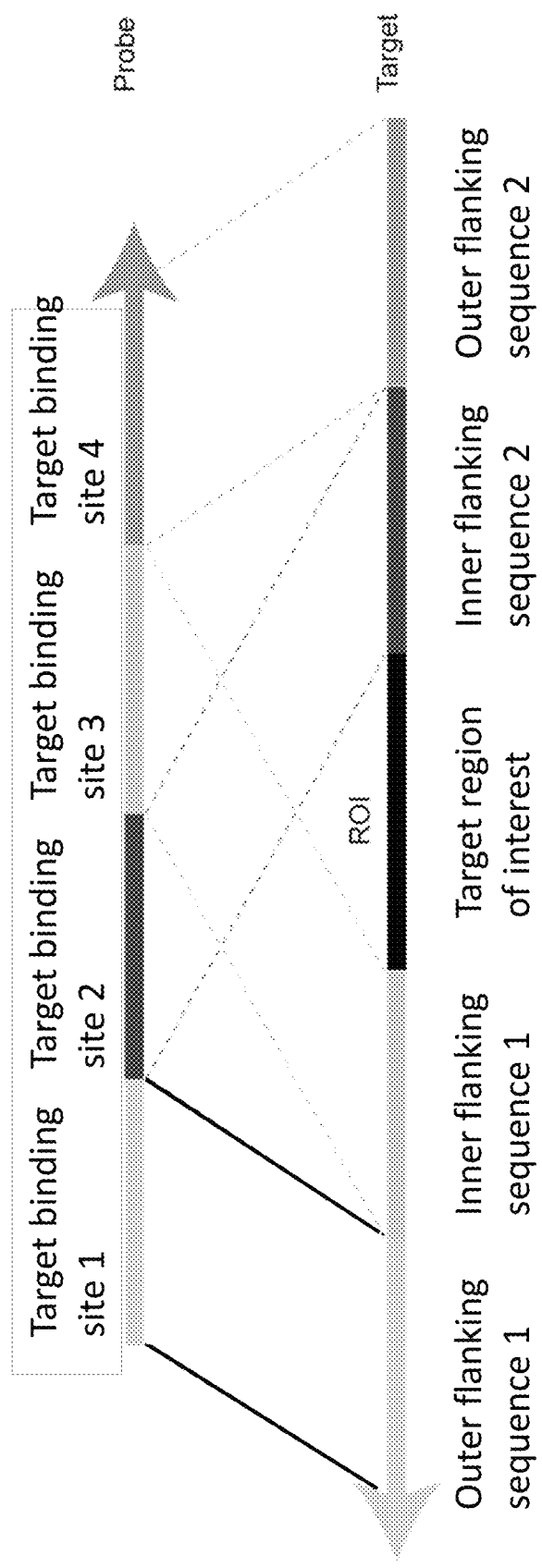

37 Claims, 15 Drawing Sheets
Specification includes a Sequence Listing.

METHOD FOR SELECTING A TARGET NUCLEIC ACID SEQUENCE

The Sequence Listing submitted herewith, entitled "Feb-1-2019-seq-list_ST25.txt", created Feb. 1, 2019 and having a size of 4808 bytes, is incorporated herein by reference.

The present invention relates to a method for selecting a target nucleic acid sequence. In particular, the present invention relates to a method of selecting a target region of interest (ROI) in a target nucleic acid molecule using a particular nucleic acid probe comprising sequences capable of directing the cleavage of a target nucleic acid molecule to release a fragment comprising the ROI and sequences capable of templating the circularisation and ligation of the target fragment. The circularised molecule thus obtained contains the selected ROI and may be subjected to further analysis and/or amplification etc. The selection method of the invention thus provides a method not only for selectively isolating or separating a desired target sequence (ROI), but also for detecting a target nucleic acid sequence (ROI), or for amplifying a target sequence (ROI).

There are several methods described for selection and subsequent amplification of selected parts of a nucleic acid. Examples include so-called selector probes (U.S. Pat. No. 7,883,849, or general circularisation of genomic fragments as described in Drmanac et al 2010. Science 327, 78-81 and U.S. Pat. No. 8,518,640).

Selector probes as described in U.S. Pat. No. 7,883,849 are designed to bind in a sequence-specific manner to a desired target sequence hence allowing it to be "selected" from a nucleic acid molecule, or indeed from a sample containing nucleic acid molecules. In the method of U.S. Pat. No. 7,883,849 partially double-stranded selector probes (either a single symmetrical molecule in which the longer strand overhangs at both ends, or two asymmetrical molecules each having a single-stranded overhang at only one end) are hybridised via their single-stranded overhangs in a target-specific manner to both ends of single-stranded (denatured) target fragments resulting from fragmentation of the nucleic acid sample. In a particular embodiment of the method using the symmetrical selector probe, only one end of the target fragment hybridises to an end of the selector probe, the other end of the selector probe hybridising internally of the target nucleic acid fragment and requiring a structure-specific endonuclease to resolve the resulting structure by cleaving off the portion of the target fragment protruding beyond the internal hybridised region. In all cases, therefore, the selected portion of the target fragment is delineated by the regions (whether both end regions or one end and one internal region) of known sequence to which the selector probe(s) has been designed to hybridise. Following hybridisation (and, where appropriate, resolution of the secondary structure) the selector(s) and target nucleic acid fragment are joined by ligation to give (i) in the case of the symmetrical selector probe, a circular nucleic acid molecule and (ii) in the case of the two asymmetrical selectors a linear molecule comprising the target fragment flanked by selector probe sequences. The double-stranded region of the selector probe(s) contains a primer pair motif which is common to the plurality of different target-specific selectors used in a multiplex assay. Hence, amplification of multiple target fragments can be achieved simultaneously whilst avoiding amplification artefacts which can result from the use of multiple, different primer pairs.

A particular problem identified in the selection methods of U.S. Pat. No. 7,883,849 is the requirement to carefully select which restriction enzymes are used to digest a target nucleic acid molecule prior to selection, in order to avoid selecting enzymes which can cleave a target nucleic acid molecule within the target sequence to be interrogated. This places limits on the degree of multiplexing that is possible according to this method, and can lead to the amplification of unduly long nucleic acid fragments, thereby increasing the cost of analysing the target nucleic acids selected.

In contrast to methods disclosed in the prior art, the present invention does not require the prior cleavage of a sample nucleic acid prior to selection (although this is not precluded), and in particular it does not require cleavage in a manner to create specific binding sites for the probe in the target molecule. Instead, it directs cleavage to particular sites within a single-stranded target nucleic acid molecule where a nucleic acid probe binds, thereby circumventing the precise selection of restriction enzymes to be used. Thus the present invention provides an improved method for the selection of target nucleic acid molecules, and allows for the more precise selection of which sequences are to be interrogated or analysed, e.g. by sequencing, but without requiring target fragments containing specific probe binding sites at their ends.

The invention accordingly provides a new kind of probe for selecting a desired or target nucleic acid sequence, which provides a new way of generating a circular molecule containing the target sequence. Circular molecules may readily be separated and handled (e.g. by digesting any linear non-circularised nucleic acid molecules using exonuclease enzymes) and may also be readily amplified and/or detected using rolling circle amplification (RCA) or other amplification procedures. They are thus a very convenient way of providing a selected target sequence for further handling or processing, or analysis or detection etc.

The new probe for use according to the invention is a single stranded nucleic acid molecule (i.e. an oligonucleotide) comprising four target-specific binding sites arranged in order, the two "outer" binding sites binding to complementary regions (or binding sites) in the target molecule which creates cleavage sites flanking the target sequence, or ROI. The two inner target-binding sites of the probe serve as templates for circularisation of the fragment which is released from the target molecule by cleavage at the created cleavage sites. Sequence elements can be placed adjacent to, or in between, the four target-binding sites to enable or facilitate various downstream applications, e.g. elements serving as tag or detection or identification sequences or sequences for the capture (e.g. immobilisation) or amplification of the target sequence/ROI, e.g. detection or ID tags or motifs (e.g. barcodes etc.), binding sites for detection probes or primers or for amplification primers, or a capture (or "anchor") sequence able to bind to a complementary sequence or cognate binding partner, e.g. provided on a solid support.

The method of the invention allows the use of single stranded target molecules and target fragments without the need to know the end-sequence of the target. However, whilst the need to create fragments with target-specific ends is avoided and the method does not require a fragmentation step, it may be convenient and desirable to include an initial fragmentation step in the method.

Advantageously, and in contrast to certain prior art methods, the original target molecule is circularised and not a copy thereof. Thus the template for a subsequent amplification will be the original molecule, which can reduce errors in sequencing or sequence analysis of the amplicon. This is particularly advantageous in the context of amplification by RCA where the original circularised molecule is the template for each round of amplification, i.e. each copy of the circle—the likelihood of an error being introduced in every lap of the RCA is very low, and particularly so at the same nucleotide position—this makes the method of the invention very attractive for sequence analysis, e.g. genotyping applications, as the error rate is almost infinitesimally low. The method thus has particular utility in the detection or identification of rare mutations and similar applications.

In a first aspect the invention accordingly provides a method of selecting a target region of interest (ROI) in a target nucleic acid molecule, said method comprising:

(a) providing a probe comprising in the following order four target-binding sites capable of hybridising to complementary binding sites in the target molecule, which complementary binding sites flank the target ROI, as follows:
  (i) a first target-binding site, complementary to a first outer flanking sequence flanking a first side of the ROI in the target molecule;
  (ii) a second target-binding site, complementary to a second inner flanking sequence flanking the other side of the ROI on the target molecule;
  (iii) a third target-binding site, complementary to a first inner flanking sequence flanking the first side of the ROI in the target molecule;
  (iv) a fourth target-binding site, complementary to a second outer flanking sequence flanking the other side of the ROI in the target molecule;
  such that only one of the second and third binding sites are able to hybridise to their respective complementary binding site in the target molecule when said first, fourth and the other of second and third binding sites have hybridised;
  wherein the first and fourth binding sites comprise a sequence capable of creating a cleavage site when hybridised to the target molecule;

(b) contacting the probe with the target molecule and allowing the first, fourth and one of the second and third target binding sites to hybridise to their respective complementary binding sites in the target molecule, wherein the target molecule is at least partially single stranded including in the region comprising the four complementary binding sites, such that when said probe has bound a partially double-stranded construct is created comprising a loop in the probe strand comprising the second or third target binding site which did not hybridise to the target molecule and a loop in the target molecule strand comprising the ROI and the complementary binding site which is complementary to the second or third target binding region of the probe which did not hybridise;

(c) cleaving the probe/target molecule construct at the cleavage sites created by hybridisation of the first and fourth target-binding sites thereby to release a target fragment comprising the ROI flanked by the first and second inner flanking sequences which are complementary to the third and second target binding regions of the probe, one of which is hybridised to its complementary binding site in the cleaved probe;

(d) allowing the second or third target-binding site of the probe which did not hybridise in step (b) to hybridise to its complementary binding site in the target fragment, thereby to bring the ends of the target fragment into juxtaposition for ligation, directly or indirectly, using the cleaved probe as ligation template;

(e) ligating the ends of the target fragment directly or indirectly to circularise the target fragment;

(f) amplifying or separating the circularised target fragment, thereby to select the ROI.

In a further aspect there is provided a probe for use in the method of the invention. More particularly, in this further aspect the invention provides an oligonucleotide probe for selecting a target ROI in a target nucleic acid molecule, said probe comprising in the following order four target-binding sites capable of hybridising to complementary binding sites in the target molecule, which complementary binding sites flank the target ROI, as follows:

(i) a first target-binding site, complementary to a first outer flanking sequence flanking a first side of the ROI in the target molecule;
(ii) a second target-binding site, complementary to a second inner flanking sequence flanking the other side of the ROI on the target molecule;
(iii) a third target-binding site, complementary to a first inner flanking sequence flanking the first side of the ROI in the target molecule;
(iv) a fourth target-binding site, complementary to a second outer flanking sequence flanking the other side of the ROI in the target molecule;

such that only one of the second and third binding sites are able to hybridise to their respective complementary binding site in the target molecule when said first, fourth and the other of second and third binding sites have hybridised; and wherein the first and fourth binding sites comprise a sequence capable of creating a cleavage site when hybridised to the target molecule.

It will be understood from the above the probe does not comprise a sequence which is capable of hybridising to the ROI.

The probe binds to the target nucleic acid molecule in a selective manner, allowing a "selected" target fragment comprising the ROI and flanking sequences to be cleaved from the target molecule and subsequently circularised by ligation of the ends of the fragment in a probe-templated ligation.

The selective cleavage is achieved by providing the probes with target binding sites (binding sites 1 and 4) which bind to regions ("complementary binding sites") flanking the ROI in the target molecule (the "outer flanking sequences" on either side of the ROI), creating cleavages sites which flank the ROI. Thus there are two outer binding sites (1 and 4) and two inner binding sites (2 and 3) in the probe corresponding to cognate outer and inner flanking sites in the target molecule, which flank the ROI. To enable the cleaved fragment containing the ROI to be circularised, a ligation template is provided by a nucleotide sequence in the probe comprising target-binding sites 2 and 3, which bind to complementary binding sites in the target molecule which flank the ROI inside the outer flanking sites (which create the cleavage sites). These complementary binding sites in the target molecule thus represent the ends of the fragment which is created by the cleavage, and their hybridisation to both the target binding sites 2 and 3 in the probe following cleavage brings the fragment ends into juxtaposition for ligation to circularise the fragment. In order for this to happen, the order of binding sites 2 and 3 in the probe is "reversed" with respect to the order in which the complementary binding sites appear in the target molecule—thus where binding site 1 binds to the outer flanking region on a first side of the ROI, binding site 2 binds to the inner flanking region on the other side of the ROI. Binding site 3 binds to the inner flanking region on the first side of the ROI and binding site 4 binds to the outer flanking on the other (second) side. This means that only one of binding sites 2 and 3 is able to hybridise to the target molecule when binding sites 1 and 4 are hybridised. In this way probe hybridisation causes the binding site 2 or 3 which has not hybridised to the target to loop out. Similarly the cognate complementary binding site in the target molecule (complementary to binding site 3 or 3 which has not bound) is caused to loop out. Further, since the probe does not comprise a sequence complementary to the ROI, this also loops out. Probe hybridisation thus results in a partially double-stranded construct comprising an unhybridised single stranded region (loop) in the probe strand comprising the unhybridised binding site 2 or 3, and a loop in the target strand comprising the ROI and the complementary binding site cognate to the unhybridised binding site 2 or 3 of the probe.

Thus three out of the four binding sites in the probe hybridise in the initial probe binding step, including the two outer binding sites. The fourth (inner) binding site is able to hybridise when it is released from the probe in the cleavage step, causing the ends of the cleaved fragment to be brought into juxtaposition for ligation. As mentioned above, the ligation may be direct, when the fragment ends are ligated directly together, or it may be indirect when the two fragment ends hybridise to their respective binding sites 2 and 3 in the probe with a space (i.e. gap) or intervening sequence between them. As will be described in more detail below, this may occur when binding sites 2 and 3 are not immediately adjacent in the probe, but are separated by an intervening sequence. In such a configuration the gap between the hybridised fragment ends may be filled, either by a "gap" oligonucleotide, which hybridises to the intervening sequence between binding sites 2 and 3 in the probe, or by extension of the hybridised 3' end of the fragment. The gap oligonucleotide may be provided pre-hybridised to the intervening sequence in the probe, or added separately, e.g. later during the method. It may also be provided in one or more parts.

The orientation of the probe is not critical and the probe may be in either orientation. Thus the binding sites 1, 2, 3 and 4 may lie 3' to 5' in the probe or 5' to 3'.

Figure 3:
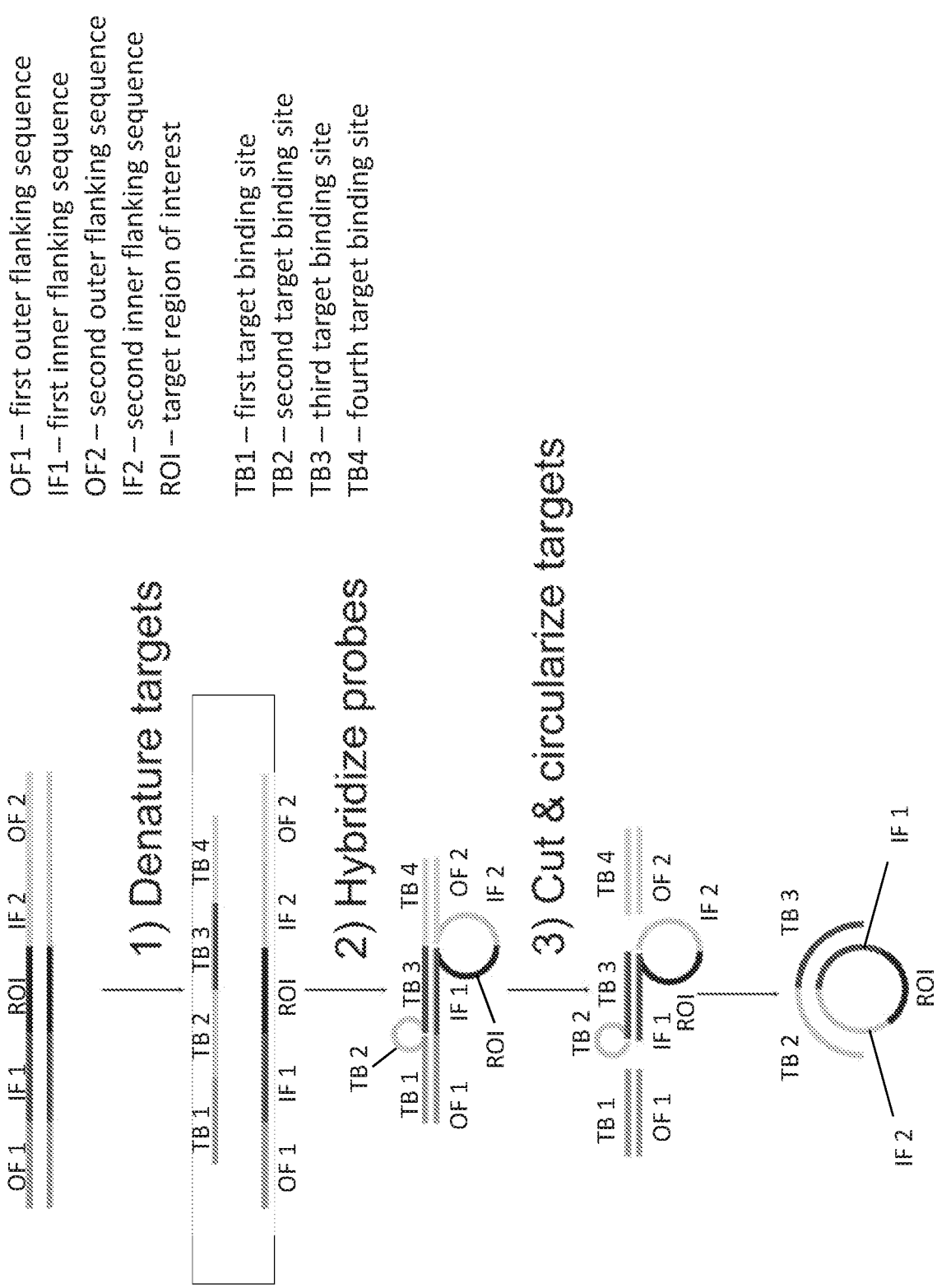

Further, the order of hybridisation of the three binding sites which hybridise in step (b) is not critical and the binding sites may hybridise simultaneously, or substantially simultaneously, and/or sequentially, in any order. In a representative embodiment, as shown in FIG. 3, binding site 2 does not hybridise in step (b) and hybridises after cleavage. However, in an alternative embodiment, binding site 2 may hybridise in step (b) and binding site 3 may hybridise after cleavage. The target ROI which is selected may be any desired sequence or subsequence in a target nucleic acid molecule. The ROI may thus alternatively be termed a "target sequence" in a target nucleic acid molecule. For example it may be a region of a nucleic acid in a sample which it is desired to amplify.

The term "selecting" is used broadly herein and includes any means of selecting, isolating and/or separating a nucleic acid sequence of interest, for example from a nucleic acid sample which contains other nucleic acid molecules, particularly other DNAs, in addition to the target nucleic acid molecule or indeed from a longer nucleic acid molecule containing the target ROI.

The target nucleic acid molecule is thus any nucleic acid molecule containing the target ROI. As will be discussed in more detail below, it may be a genomic molecule or a fragment thereof, or any kind of synthetic or artificial nucleic acid molecule. Thus "selecting" encompasses any means of practically, if not actually physically, "separating" the target ROI from the other nucleic acids present in a sample, and/or from the rest of the target molecule. The selected ROI contained in the circularised target fragment may be subjected to amplification, e.g. by one of the many known methods of nucleic acid amplification, to amplify the ROI, for example for detection of the ROI or to enable further analysis, e.g. by sequencing, or to physical separation, e.g. capture, for example by immobilisation to a solid phase, optionally followed by amplification.

The method of the invention may thus include a further step of analysing the circularised target fragment or an amplicon thereof. As will be described further below, this may be by sequencing, or by a method of sequence analysis (e.g. detecting the presence or absence of a sequence variant or a particular nucleotide(s) in the ROI or determining the methylation status of the ROI), or by hybridisation of a detection probe to the ROI, optionally with further detection and/or signal amplification steps.

Such an analysis step will allow a target ROI to be detected, for example in a sample containing nucleic acids. The target ROI may therefore in one embodiment be a target analyte.

Accordingly, in a still further aspect the invention can also be seen to provide a method of detecting a target ROI, for example using a probe of the invention to bind to a target nucleic acid molecule containing the ROI and to select the target ROI as hereinbefore described.

The term "detecting" is also used broadly herein and includes any means of identifying, detecting or determining or assaying for the presence of the target ROI, or any means of analysing the target ROI. Direct analysis of the target ROI (i.e. sequencing of all or any part of the target ROI) is encompassed by the term "detecting".

The method of the invention may be performed in "simplex" format to enrich for a single target ROI (i.e. a single species of target ROI, which will normally be present in many copies) or for a plurality of target ROIs which are sufficiently similar in sequence, or flanked by sufficiently similar sequences so as to be possible to select them using the same probe. In this context it will be seen that the term "single" as used in relation to the probe means single in the context of a particular target ROI, namely that one probe (or more particularly one type or species of probe) is used for each target ROI (i.e. a single probe per target ROI). It is clear from the above that "single" probe means single species of probe and does not imply any limitation on the actual number of probe molecules used.

Alternatively, a plurality (i.e. a plurality of species) of probes may be used in a "multiplex" format simultaneously to enrich for a plurality of target ROIs, which may be in the same, or more typically, in different, target molecules. Hence, in such a latter aspect the method as defined above is for selecting a plurality of target ROIs, wherein a plurality of probes is provided, each designed to select a different target ROI. In such an embodiment each probe may have a different set of target-binding sites, i.e. the probes have different target-specificities. In such a multiplex method, for each target ROI of the plurality (i.e. each different type or species of target ROI) a single (i.e. in the sense of a single species of) probe may be used. Thus, a plurality of probes may be used, with a (different) probe for each target ROI. Thus in one embodiment each probe has different target binding sites, whereby a plurality of different target nucleic acid molecules (and thus a plurality of different target ROIs) may be selected. In another embodiment, different ROIs in the same target molecule may be selected. In a still further embodiment, the same probe (i.e. comprising a single set of target binding sites) may be used to detect a plurality of different target ROIs that might be present within the same target nucleic acid molecule derived from a plurality (variety) of different sources.

The term "plurality" as used herein means 2 or more (or at least 2), more particularly 3 or more (or at least 3), or 4, 5, 6, 8, 10, 15, 20, 30, 50, 70 or 100 or more etc. In certain embodiments even higher numbers of probes may be used and very many different target ROIs may be selected, e.g. 500, 1,000, 2,000, 5,000 or 10,000 or more. For example, 10, 100, 1,000 or 10,000 different probes may simultaneously be used to detect or enrich for, respectively, 10, 100, 1,000 or 10,000 different target ROIs.

The target ROI may be any sequence it may be desired to detect, analyse or amplify, for example a nucleotide sequence or a nucleic acid or selected part thereof in a pool of nucleic acid molecules or nucleotide sequences, for example genomic nucleic acids, whether human or from any source, from a transcriptome, or any other nucleic acid (e.g. organelle nucleic acids, i.e. mitochondrial or plastid nucleic acids), whether naturally occurring or synthetic. The target nucleic acid molecule may therefore be any kind of nucleic acid molecule. Thus it may be DNA or RNA, or a modified variant thereof. Thus the nucleic acid may be made up of ribonucleotides and/or deoxyribonucleotides as well as synthetic nucleotides that are capable of participating in Watson-Crick type or analogous base pair interactions. Thus the nucleic acid may be or may comprise, e.g. bi-sulphite converted DNA, LNA, PNA or any other derivative containing a non-nucleotide backbone. The target molecule or ROI may thus be coding or non-coding DNA, for example genomic DNA or a sub-fraction thereof, or may be derived from genomic DNA, e.g. a copy or amplicon thereof, or it may be cDNA or a sub-fraction thereof, or an amplicon or copy thereof etc. Alternatively, the ROI or target molecule may be or may be derived from coding (i.e. pre-mRNA or mRNA) or non-coding RNA sequences (such as tRNA, rRNA, snoRNA, miRNA, siRNA, snRNA, exRNA, piRNA and long ncRNA). The probe may similarly be composed of or may comprise any nucleic acid as detailed above.

The sequence of the target ROI may not be known, providing that the sequence of the regions flanking the target ROI are known in order to facilitate the design of the probe, which must be able to hybridise to the flanking regions as defined and explained above.

The size of the target ROI is not critical and may vary widely. Thus in one embodiment of the present invention the target ROI may be at least 10 nucleotides, and preferably at least 15 nucleotides in length. Thus the target ROI may be at least 20, 25, 30, 40, 50, 60, 70, 80 or 90 nucleotides in length. It is also anticipated that the present method may be used to select a longer target ROI, for example where the target ROI is at least 100, 150, 200, 300, or 400 nucleotides in length, or up to 500, 1,000, 1,500, 2,000, 2,500, 3,000, 5,000, 10,000, 25,000, 50,000 or 100,000 nucleotides in length. Although RCA of nucleic acid circles may become less efficient as the size of the circle increases (e.g. above 5,000 or 10,000 nucleotides) it is still feasible. Thus representative ranges of ROI length include from any one of 10, 12, or 15 up to any one of 100,000, 50,000, 10,000, 5,000, 2,000, 1,000, 800, 750, 700, 600 or 500 nucleotides. In particular embodiments, the size range may be from any one of 10, 12, or 15 to any one of 500, 400, 300, 200, 100 or 50 nucleotides.

The target nucleic acid molecule may be present within a sample. The sample may be any sample which contains any amount of nucleic acid, from any source or of any origin, from which it is desired to select a target ROI. A sample may thus be any clinical or non-clinical sample, and may be any biological, clinical or environmental sample in which the target nucleic acid molecule may occur. More particularly, the sample may be any sample that contains nucleic acid. The target nucleic acid molecule may occur in single-stranded or partially single-stranded or in double-stranded form. However, as noted above for the practice of the method the target molecule needs to be single-stranded at least in the regions where the probe hybridises. Where necessary, the method may therefore comprise a step of rendering the target nucleic acid at least partially single-stranded, as discussed further below.

In one embodiment of the above method, the target ROI may be detected in situ, as it naturally occurs in the nucleic acid molecule in the sample. In such an embodiment the target nucleic acid molecule may be present in a sample at a fixed, detectable or visualisable position in the sample. The sample will thus be any sample which reflects the normal or native ("in situ") localisation of the target nucleic acid molecule, i.e. any sample in which it normally or natively occurs. Such a sample will advantageously be a cell or tissue sample. Particularly preferred are samples such as cultured or harvested or biopsied cell or tissue samples in which the target ROI may be detected to reveal the localisation of the target ROI relative to other features of the sample. As well as cell or tissue preparations, such samples may also include, for example, dehydrated or fixed biological fluids, and nuclear material such as chromosome/chromatin preparations, e.g. on microscope slides. The samples may be freshly prepared or they may be prior-treated in any convenient way such as by fixation or freezing. Accordingly, fresh, frozen or fixed cells or tissues may be used, e.g. FFPE tissue (Formalin Fixed Paraffin Embedded).

Thus, representative samples may include any material which may contain a target nucleic acid molecule, including for example foods and allied products, clinical and environmental samples etc. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include clinical samples, e.g. whole blood and blood-derived products such as plasma, serum and buffy coat, blood cells, other circulating cells (e.g. circulating tumour cells), urine, faeces, cerebrospinal fluid or any other body fluids (e.g. respiratory secretions, saliva, milk, etc.), tissues, biopsies, as well as other samples such as cell cultures, cell suspensions, conditioned media or other samples of cell culture constituents, etc.

Although the method of the present invention may be used to select a target ROI in a target nucleic acid molecule in an in situ (i.e. a native) setting, it is also contemplated that the method may be employed to select a target ROI in a target nucleic acid molecule in an in vitro detection system, i.e. where a target nucleic acid molecule has been isolated or purified from its native setting. The sample may thus be a direct product of a nucleic acid isolation procedure, or of a cell lysis procedure, or it may further be fractionated or purified in some way, e.g. it may contain nucleic acids which have been partially or fully separated. The sample may also be treated in any way, e.g. the cDNA reverse transcript of an RNA molecule.

Although a fragmentation step is not necessary, it may in the case of certain target nucleic acid molecules or certain samples, e.g. in the context of genomic DNA, be desirable or convenient to include a fragmentation step in the method, such that the nucleic acid in the sample, or the target molecule, is fragmented prior to the hybridisation of the probe. This may occur prior to or at the same time, or substantially the same time, as contacting the sample, or the target nucleic acid molecule with the probe. As mentioned above, where the target molecule is double-stranded, a step of rendering the molecule at least partially single-stranded is required. This step may be separate to the fragmentation step, e.g. after fragmentation, but may occur as part of the fragmentation step. Fragmentation may be required or helpful in order to allow the at least partially single-stranded nucleic acid to be prepared.

The term "fragmenting" is used broadly herein to include any means by which the nucleic acid in the sample, or more particularly the target molecule, may be fragmented or cleaved. Thus, fragmentation may be carried out enzymatically, e.g. using restriction or other endonucleases or nucleases such as DNase, and/or physically, e.g. by nebulisation or sonication or any shear-based methods. Such physical methods result in unpredictable, non-sequence-specific fragmentation, as do certain (non-restriction) endonucleases. Thus both random, and pre-determined (or site-specific) fragmentation is encompassed, but the latter is not necessary. Also encompassed by "fragmenting" is fragmentation of a nucleic acid sample which inherently may occur as a result of the age of a sample, the conditions in which it is stored and any treatment of the sample (e.g. fixation, such as in formalin-fixed paraffin-embedded samples), and the degradation to which these factors contribute. Any suitable class of restriction endonuclease may be used, including type II and type IIs enzymes. Alternatively, fragmenting may be achieved using a flap endonuclease (FEN), wherein an added nucleic acid or oligonucleotide is used to create a structure which is a substrate for such as structure-specific endonuclease, i.e. a structure having a protruding non-hybridised 5' end region. Fragmenting means may be used in combination, e.g. the use together of two or more endonucleases, more particularly two or more restriction endonucleases, or the use together of an enzymatic and a physical means. Furthermore, the nucleic acid sample may be differently fragmented in separate aliquots, which aliquots are then pooled and together subjected to the remaining steps of the method of the invention. In certain cases, it may be appropriate and sufficient to fragment using a single restriction endonuclease, but in other cases the use of additional restriction endonucleases may be preferred.

Hence, the fragmenting may be achieved by separating the nucleic acid sample into a plurality of aliquots and fragmenting the respective aliquots with different means or different combinations of means, such means being for example restriction enzymes. Any number of aliquots of the sample may be differently treated, e.g. 2 or more, or 3, 4, 5, 6, 7, 8, 9, 10, 11, 12, 13, 14, 15 or 20 or more etc. The aliquots are then subjected to the remaining steps of the method and may be pooled for example before step (b).

Before the target molecule can hybridise with the probe, it must be at least partially single-stranded. This may be achieved, if necessary, by any means known in the art, such as denaturation, e.g. by heat or pH, or through the use of chemicals, e.g. alkali. Heat denaturation is preferred.

Thus, after or concomitantly with any fragmenting step, the nucleic acid in the sample, including the target nucleic acid molecule, may if necessary be rendered at least partially single-stranded, to allow probe hybridisation in step (b) to occur. Where the nucleic acid molecule is not made completely single-stranded, it is required that it is single-stranded at least the portions which comprise the probe-complementary portions (so as to allow binding to the probe). As well as by denaturation, at least partial single-strandedness can be achieved by 3' or 5' exonucleolysis using an appropriate 3' or 5' exonuclease. Starting at a free double-stranded fragment end, such enzymes progressively degrade or digest one strand of a double-stranded nucleic acid, leaving the complementary strand and rendering the nucleic acid single-stranded along the length of the enzyme's action. The extent of exonucleolytic degradation (i.e. the length of the resulting single-stranded region) may be controlled by the duration of the reaction. The duration of the exonuclease reaction is chosen in order that an appropriate length of one end of the strands of the fragments is removed. The extent of digestion must be sufficient to allow hybridisation with the probe. Suitable exonucleases are known in the art and include, e.g. exonuclease III (3') and lambda exonuclease (5').

Figure 6:
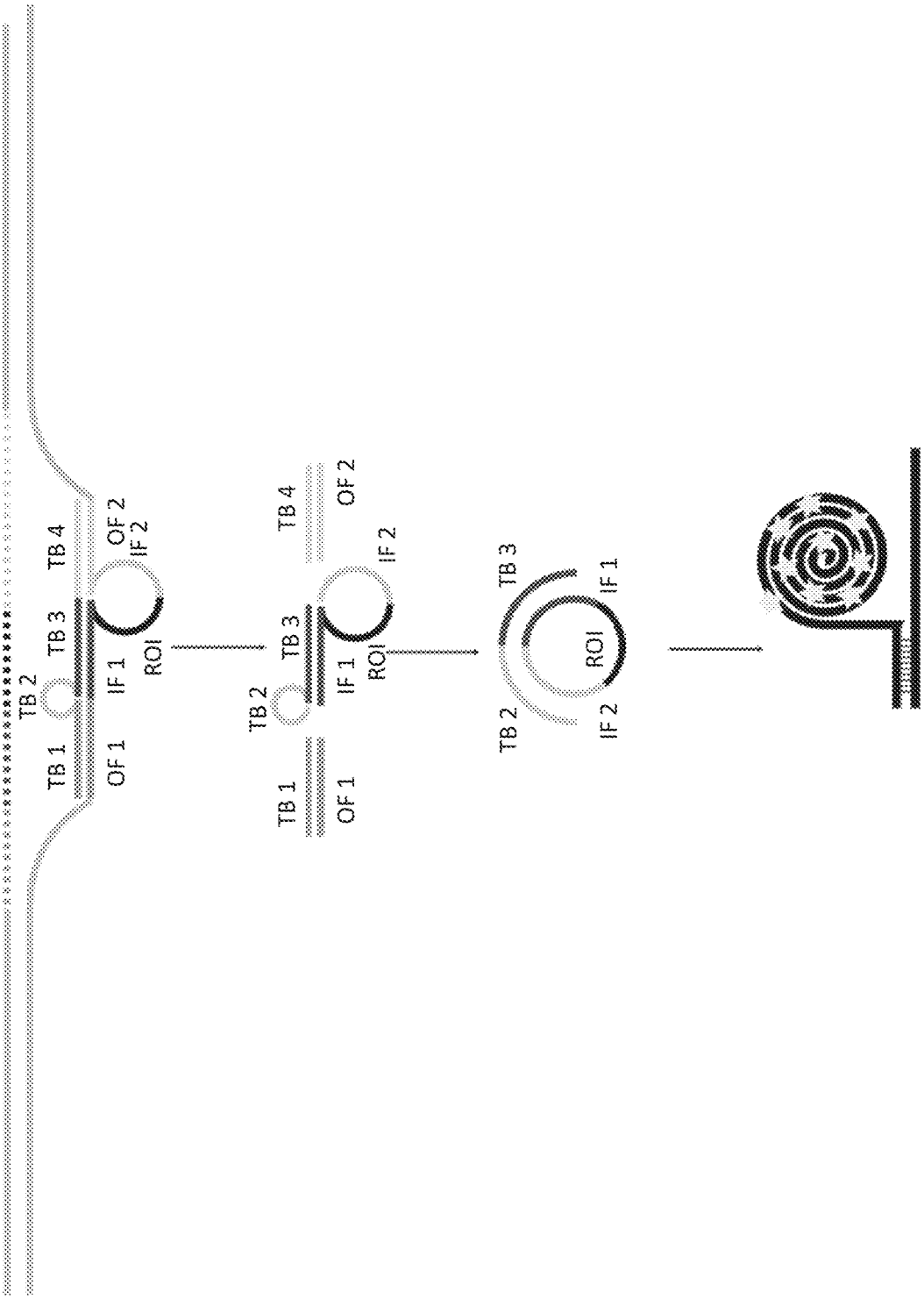

Further, in certain applications, for example in situ procedures as shown in FIG. 6, the duplex of a target nucleic acid molecule may be opened up to permit probe hybridisation, without fully denaturing the nucleic acid. Procedures for this are known in the art. In some embodiments, the circularised target fragment may be detected by RCA, wherein it may be useful to facilitate localisation of the RCA product to its native position, e.g. such that the RCA product functions as a localised marker for the target nucleic acid molecule in the sample. For instance, the RCA product may be localised to the sample by immobilising the RCA product to the target nucleic acid or in proximity to the target nucleic acid. Methods for immobilising the RCA product are described further below and could be used to immobilise the RCA product in situ, e.g. wherein the nucleic acid molecule used to immobilise (e.g. capture or anchor) the circularised target fragment is immobilised to a specific location in the sample, e.g. the receptor or binding oligonucleotide, may consist of, or be attached to, an affinity binding molecule that is capable of interacting with its cognate binding partner (e.g. the target nucleic acid molecule), which is located in the sample, e.g. the cell.

The probe may therefore comprise a capture or anchor element, e.g. a capture or anchor sequence or an affinity binding group, that may be used to immobilise or localise the circularised fragment, or more particularly, an amplification product thereof, to a specific location e.g. in a cell. Such a capture or anchor element may be provided in (e.g. as part of, or attached to) the second or third target-binding sites of the probe, or an intervening sequence adjacent thereto, such that it is present in the portion of the probe which templates the ligation of the target fragment comprising the ROI following cleavage of the probe. The capture or anchor element may bind to a molecule (i.e. its cognate binding partner) present in the sample (e.g. in the cell), including for example the target nucleic acid molecule itself. In one embodiment, a capture or anchor sequence may hybridise to a portion or part of the target nucleic acid molecule. Whilst this may not be the target ROI or a flanking region thereo, it may be a nucleic acid sequence adjacent or near to the ROI. Where the portion of the probe which templates ligation comprises the capture or anchor sequence and also acts as the primer for RCA, the amplification product may be localised to the location of the target molecule. In particular, the amplification product may be bound (hybridised) to the target nucleic acid molecule by virtue of the capture or anchor sequence.

In some embodiments it is not necessary to actively immobilise the RCA product, e.g. to the target nucleic acid molecule, in order to produce a localised signal in situ. In this respect, whilst not wishing to be bound by theory, it is hypothesized that the RCA product rapidly becomes too large to readily diffuse away from its source, i.e. the RCA product is localised in its cell of origin even though it may not be directly or indirectly immobilized, e.g. to, or in proximity to, the target nucleic acid.

A number of different designs may be employed for the probe of the present invention. At its simplest, as depicted in FIGS. 1 and 3, the probe is a linear molecule comprising four target binding sites capable of hybridising to complementary binding sites in the target molecule as defined above, wherein the four target binding sites are immediately adjacent to one another. Thus the two outer binding sites 1 and 4 lie at the ends of the probe.

In variant embodiments, the probe may comprise at least one (i.e. one, two, three or more) intervening sequence between any of the four target binding sites. One or more intervening sequences may be present between any two of the target binding sites within the probe, and multiple intervening sequences may thus be present within the probe, interspersed between the various target binding sequences. As noted above these may be used to introduce elements useful for or which facilitate downstream processing or handling, for example to introduce tag or detection sequences or elements allowing the probe and/or circularised fragment to be captured, for example for immobilisation to a solid phase. Thus the probe may comprise an intervening sequence between the first and second target binding sites, and/or an intervening sequence between the second and third target binding sites, and/or an intervening sequence between the third and fourth target binding sites. In a further embodiment, the nucleic acid probe may comprise intervening sequences between both the first and second target binding sites, and between the third and fourth target binding sites. Alternatively, the nucleic acid probe may comprise intervening sequences between any of the first, second, third and fourth target binding sites, such as between the first and second, and second and third target binding sites; between the second and third, and third and fourth target binding sites; or between the first and second, second and third, and third and fourth target binding sites. It is also possible for a probe to comprise more than one intervening sequence between any two target binding sites. The nucleic acid probe may also comprise additional sequences beyond the first and/or fourth target binding site. Importantly, neither the intervening sequences, nor the additional sequences are capable of hybridising to the target nucleic acid molecule.

From the probe design it will be apparent that any intervening sequence incorporated between binding sites 2 and 3 will result in there being a gap between the hybridised ends of the cleaved target fragment. As noted above, this gap needs to be filled in order for ligation of the ends to take place. Such an intervening sequence may therefore be used to introduce a sequence into the circularised target molecule, for example a tag or detection sequence, e.g. a barcode or identificatory motif, or a binding site for a detection probe or primer. Tags such as barcodes/motifs or probe/primer binding sites may be designed with different needs/purposes, for example to introduce a universal or common sequence to enable different circularised target molecules in a multiplex setting to be processed together, e.g. to introduce a binding site for a universal or common amplification primer. This would enable different circularised target fragments to be amplified together, e.g. in a library amplification by PCR or RCA. Alternatively or additionally, a tag/barcode sequence may be used to "label" different circularised fragments so that they may readily be distinguished from one another (i.e. a "target" tag or marker), or to tag different samples etc., so that they may be pooled prior to common/universal amplification together (i.e. a "sample" tag or marker). Thus, in a multiplex setting different probes (i.e. probes for different target ROIs) may be provided with different tag sequences (e.g. different marker or detection sequences) and/or they may be provided with the same tag sequence(s), e.g. for the introduction of a common or universal sequence.

As mentioned above, gap-filling may take place either by extending the hybridised 3' end of the target fragment, or more typically by hybridising one or more gap oligonucleotides into the gap. The gap oligonucleotide may be provided as part of the probe (see e.g. FIG. 2B, 2D or 4), e.g. prehybridised to the probe prior to contact with target nucleic acid, or it may be provided at the same or substantially the same time as contacting the probe with the target molecule, or it may be added at any time afterwards, e.g. after probe hybridisation, or after cleavage. The gap oligonucleotide may therefore be regarded as a detection, tag, barcode or ID motif oligonucleotide etc. As will be described in more detail below and as depicted in FIG. 2D the gap oligonucleotide may comprise a region which is not complementary and does not hybridise to the intervening sequence between binding sites 2 and 3 such that when it is hybridised it contains a non-hybridised loop into which a tag, barcode, or ID motif sequence etc. may be incorporated.

Figure 2:
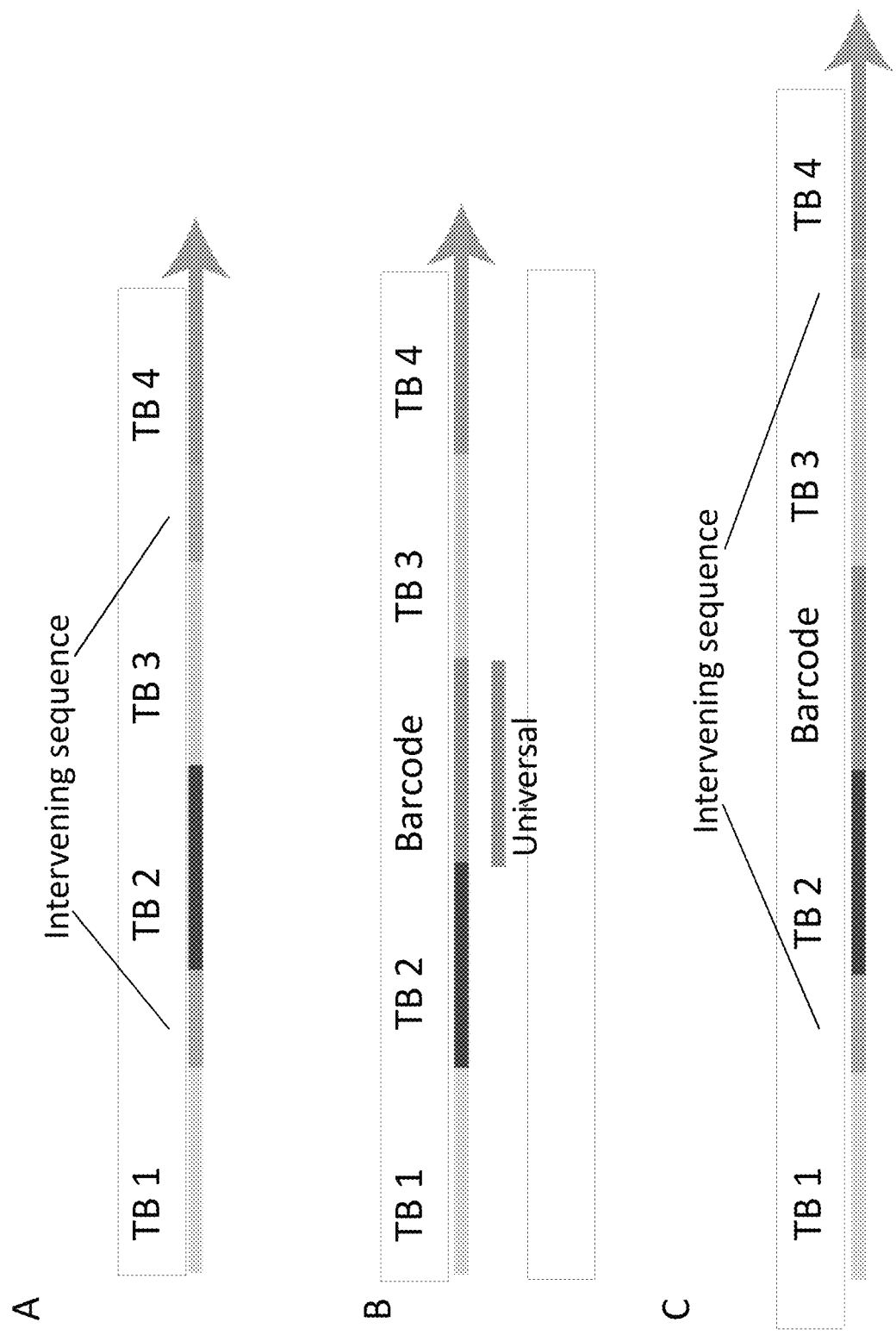

In a further embodiment, capture or "anchor" sequence elements may be placed between two binding sites, for example between binding sites 1 and 2 and/or between binding sites 2 and 3, and/or between binding sites 3 and 4. Such elements may be combined with detection/ID elements between any of the sites. For example, capture elements between site 1 and 2, 2 and 3, and 3 and 4 respectively may be combined with a detection/ID element between sites 2 and 3. Various representative possibilities are depicted in FIG. 2. Such capture or anchor elements may be designed to hybridise to a cognate complementary binding site (i.e. a "bait" sequence), for example provided on a solid support, to enable the probe and/or target fragment to be immobilised. This may thus enable the method to be carried out on a solid phase for one or more of the steps, for example the probe may be immobilised before or after hybridisation to the target molecule, or before or after the cleavage step. This is depicted in more detail in FIG. 5.

Thus the intervening sequence(s) may contain or carry an element by which the target fragment may be detected or separated, e.g. identified or amplified or captured. By "contains or carries" is meant that such an element may be contained within the nucleotide sequence of the oligonucleotide, e.g. a sequence tag (e.g. which can be used to identify a target fragment) or a probe or primer binding site or other nucleic acid-based affinity-binding site (for example a binding site for a hybridisation probe or for a DNA binding protein etc., which binding site may be viewed as a capture or detection element depending on the nature of the probe or affinity binding element, or a binding site for a sequencing primer, which sequencing primer binding site may accordingly be viewed as a detection element, or for an amplification primer, which amplification primer binding site may accordingly be viewed as an amplification element), may be contained within the nucleotide sequence of the oligonucleotide. Alternatively it may be attached or conjugated or in any way linked or coupled to or associated with the intervening sequence. For example, it may be a functional moiety (e.g. a chemical group or a molecule) which is attached etc. to the oligonucleotide, such as an immobilisation moiety or a detection moiety (e.g. a reporter or a label). An immobilisation moiety may, for example, be an affinity binding moiety or group, e.g. one member of an affinity binding pair (i.e. an affinity ligand), which is attached or conjugated etc. to said oligonucleotide, and is capable of binding to the other member of the affinity binding pair (i.e. its cognate binding partner) for the purposes of capture or separation, e.g. when the cognate binding partner is attached to a solid phase.

A detection element may, for example, include an identification element, namely an element which allows or permits identification, for example of a particular target ROI, or of a sample (e.g. when samples are pooled), or indeed of an individual target nucleic acid molecule in the sample. Such an identification element or ID tag or motif may simply be a sequence tag or motif, e.g. a particular or unique nucleotide sequence. This may thus be viewed as a sequence marker. The design of such sequence tags/motifs or markers is well known in the art. For example barcode sequences/motifs for use as tags are widely used and known in the art, for tagging samples or molecules etc. Degenerate sequences may be used as the basis for such tags and again the use of degenerate sequence motifs in this way is known in the art.

A number of different tags may be included to mark or tag different aspects of the target nucleic acid molecule or ROI. For example a tag, e.g. a barcode motif, may be included as a sample tag, together with a tag for the particular target ROI for which the probe is designed to be selective. Advantageously, a "molecular" tag may be used to mark or tag (i.e. identify) an individual molecule in the sample, e.g. an original molecule of the sample. This can be particularly advantageous in the context of sequencing, and especially in NGS technologies, where it can be valuable to track sequence reads back to an original, molecule which is amplified for sequencing.

Thus, it will be seen that various types of identification element or tag may be used singly or in combination.

Sequence tag or barcodes can be in the region of 20 nucleotides, for example from 7 to 30 nucleotides, e.g. 7, 8, 9, 10, 11, 12, 13, 14, 15, 16, 17, 18, 19, 20, 21, 22, 23, 24, 25, 26, 27, 28, 29 or 30 nucleotides, in length. Sequence tags or barcodes can be randomly generated, for example a set of sequence tags may comprise tags with all possible sequence combinations of the total number of nucleotides in the tag sequence.

Thus, the probe may contain a sample sequence tag, e.g. a feature which allows a probe used in the method of the invention as performed on a particular sample to be distinguished from a probe used in the method as performed on a different sample and which thereby allows identification of the sample from which a given target fragment has been circularised.

The sample tag allows identification of the sample from which a particular target fragment and hence ROI originates. The samples may, for example, correspond to patient samples. If the method is performed in multiplex for detection of a number of different target ROIs from different samples, then separate sample and "target" tags may be included in each probe. Utilising the methods and probes of the present invention, this feature advantageously allows the pooling of samples, for example after contact with the probes and ligation of the probes to tag each sample, different samples may be pooled.

A detection element may, as noted above, also be a binding site contained in the oligonucleotide sequence (e.g. a binding site for a detection probe or moiety or for a primer to be used in a detection reaction, e.g. a sequencing primer) or it may be a detection moiety which is carried in any way by the oligonucleotide, e.g. a reporter group or moiety or a label, which may be directly or indirectly signal-giving. For example it may a visualisable label, such as a coloured or fluorescent or particulate label (e.g. a magnetic or paramagnetic particulate label), or a moiety which contributes to or takes part in a signal-giving reaction, e.g. an affinity binding partner or ligand or a substrate or co-factor for an enzyme.

A capture element may be any element for the amplification and/or capture of the circularised target fragment. An "amplification element" may be used to amplify the circularised target fragment. Typically it will be an amplification primer binding site. It may also be a binding site for one of a number or set (e.g. pair) of amplification primers, for example to allow exponential amplification, e.g. a PCR primer or a primer for a PCR-based procedure. The primer binding site may also be used for the binding of a sequencing primer.

A "capture element" may be any moiety carried by (e.g. attached or conjugated to etc.) the probe (particularly the circularised target fragment/probe construct), or any feature of the sequence of the probe (e.g. a binding site, intervening sequence), which may potentially be used selectively to attach a probe (particularly the circularised target fragment/probe construct)) to a solid phase or support, including for example a particle such as a bead. Hence, a capture element may be viewed as an "immobilisation element". Numerous examples of such elements are known in the art and include, e.g., an affinity binding partner, e.g. biotin or a hapten, capable of binding to its binding partner, i.e. a cognate binding partner, e.g. streptavidin or avidin, or an antibody, provided on the solid phase or support. A capture element may be a nucleotide sequence with complementarity to a corresponding "binding" or "receptor" oligonucleotide or nucleotide sequence provided on the solid support. Said interaction between the probe (particularly the circularised target fragment/probe construct) and a solid phase (e.g. via an immobilised binding or receptor oligonucleotide) may particularly be mediated by click chemistry (Kolb H C et al, Angew Chem Int Ed Engl. 2001 Jun. 1; 40(11):2004-2021).

The solid phase may be any of the well-known supports or matrices which are currently widely used or proposed for immobilisation, separation etc. These may take the form of particles (e.g. beads which may be magnetic, paramagnetic or non-magnetic), sheets, gels, filters, membranes, fibres, capillaries, or microtitre strips, tubes, plates or wells etc. The support may be made of glass, silica, latex or a polymeric material. Suitable are materials presenting a high surface area for binding of the analyte. Such supports may have an irregular surface and may be, e.g. porous or particulate, e.g. particles, fibres, webs, sinters or sieves. Particulate materials, e.g. beads, are useful due to their greater binding capacity, particularly polymeric beads. Conveniently, a particulate solid support used according to the invention will comprise spherical beads. The size of the beads is not critical, but they may, e.g. be of the order of diameter of at least 1 and preferably at least 2 μm, and have a maximum diameter of preferably not more than 10, and e.g. not more than 6 μm. Monodisperse particles, that is those which are substantially uniform in size (e.g. size having a diameter standard deviation of less than 5%) have the advantage that they provide very uniform reproducibility of reaction. For example, to aid manipulation and separation, magnetic or paramagnetic beads are advantageous. Other solid phases include very small particles which can efficiently contact a high proportion of the immobilisable oligonucleotides. Such particles may further be useful by retarding the movement of particle-attached target fragments through a gel, allowing separation from free, non-particle-attached (non-target) fragments. Alternatively, also preferred is the use of a chromatographic matrix modified with groups that can be reacted covalently or non-covalently with capture elements in the probe.

Figure 4:
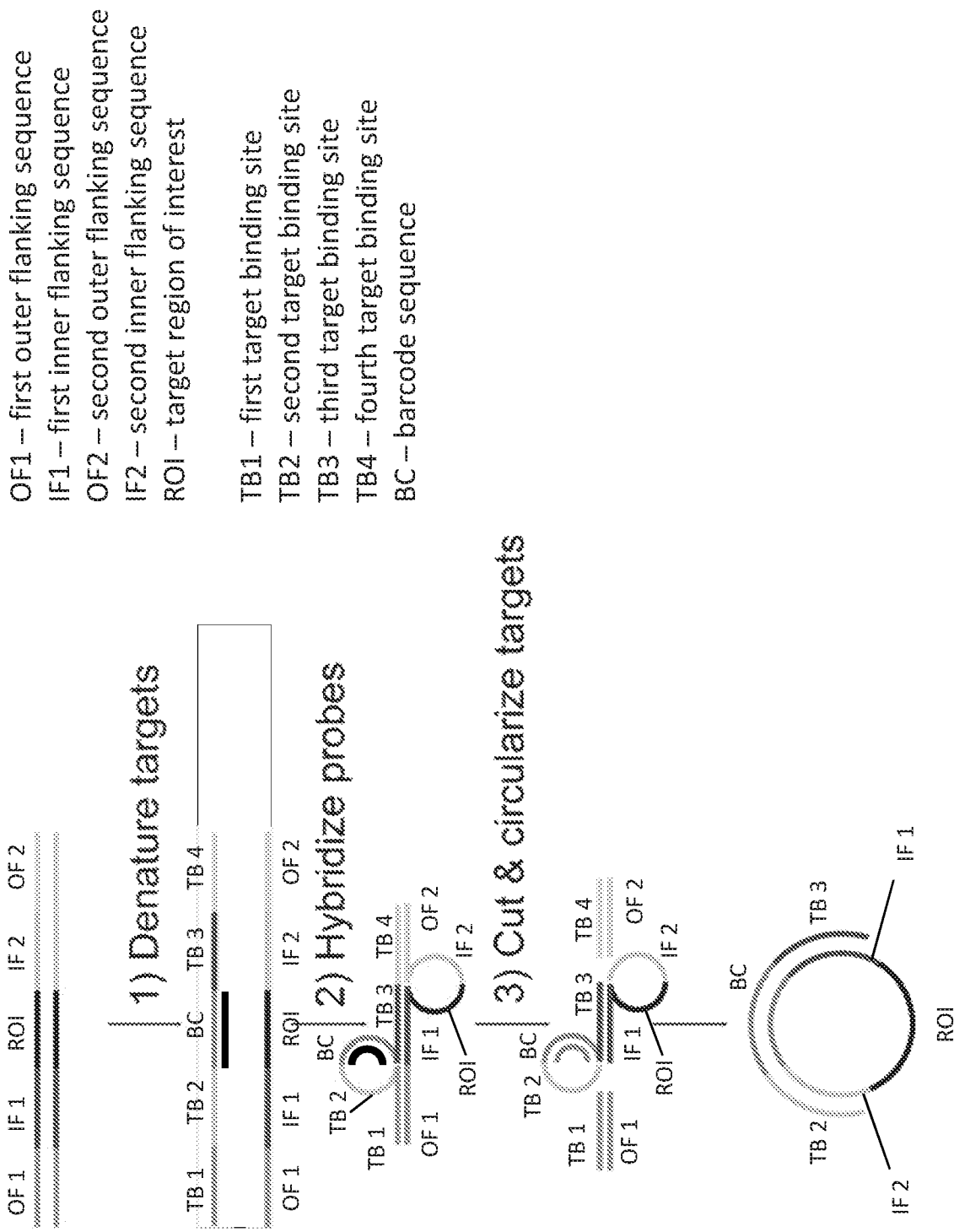

FIG. 4 depicts the operation of a probe containing an intervening sequence between binding sites 2 and 3, and comprising a hybridised tag (barcode) sequence.

As described above, and depicted particularly in FIG. 2D, the "gap" oligonucleotide which is hybridised to the intervening sequence between binding sites 2 and 3 contains regions of complementarity to the intervening sequence, which regions are separated by a sequence that is not complementary to the intervening sequence. Hence, the two regions of complementarity to the intervening sequence are at the ends of the complementary oligonucleotide, and flank a region within the oligonucleotide that is not complementary to the intervening sequence. Consequently, the sequence that is not complementary to the intervening sequence forms a loop or bulge and may comprise a tag, for example a barcode sequence etc., e.g. for identifying a selected target ROI.

In all such embodiments described above the probe is linear and the two outer binding sites (binding sites 1 and 4) lie at the ends of the probe. Such a configuration represents one preferred embodiment of the invention.

In a further embodiment, a probe may be provided which comprises a hairpin structure, and wherein it is necessary to first unfold the probe to open the loop before it can be used in the methods of the invention. The loop of the hairpin may contain one or more binding sites such that they are not available for hybridisation to the target molecule until the probe has been activated by opening, or unfolding, the hairpin to expose, or release the binding site(s). For example binding sites 1 and 2 may be contained in the loop, as depicted in FIG. 2E. Such a probe design may be helpful in the preparation of large probe libraries. A hairpin structure may also be known as a hairpin-loop or a stem-loop and these terms are used interchangeably herein. A hairpin is an intra-molecular base-pairing pattern that can occur in a single-stranded DNA or RNA molecule. A hairpin occurs when two regions of the same strand, usually complementary in nucleotide sequence when read in opposite directions, base-pair to form a double helix (a duplex) that ends in an unpaired, i.e. single-stranded, loop. The resulting structure can be described as lollipop-shaped.

Thus in the present method a hairpin may be formed by the hybridisation of two regions of the probe. In a particular embodiment, the probe may comprise one or more intervening sequences or additional sequences, which may allow the formation of a hairpin structure by hybridising either to one of the four binding sites within the probe, or by hybridising to another intervening sequence or additional sequence present in the probe. Advantageously the stem of the hairpin may be formed between an intervening sequence between binding sites 2 and 3 and an additional sequence provided at the end of binding site 1. In such an embodiment cleavage of the loop at or near to the junction between binding site 1 and the additional sequence in the stem duplex may release binding sites 1 and 2 and make them available for hybridisation, whilst retaining the additional sequence hybridised to the intervening sequence—the additional sequence thus forms a tag, detection, or barcode oligonucleotide etc. (i.e. a gap oligonucleotide). This is depicted in FIG. 2D.

Depending on the exact nature of the hairpin probe design, the hairpin may be unfolded or "opened" in various ways including by disruption of the duplex of the hairpin structure, or by cleavage, e.g. in or near the loop. As described above, it may be advantageous to retain the double stranded element of the hairpin structure and to cleave the loop of the hairpin structure. A discussion of the techniques which may be employed to unfold a hairpin structure is provided in WO2012/152942, which is incorporated herein by reference in its entirety. As discussed below, cleavage is preferably enzymatic cleavage.

As mentioned above, unfolding may also be achieved by disrupting at least part of the double stranded element of the hairpin structure. This may be achieved by altering the conditions of the sample such that the hairpin structure is no longer a thermodynamically favourable structure, e.g. by altering the temperature or salt concentrations of the solution. Similarly, the hairpin structure may be destabilised by modification of one or more of the nucleotide bases in the duplex to disrupt the hydrogen bonds (so-called Watson-Crick base pairing) which anneal the two strands. For example, cleavage of the base from the nucleotide may be sufficient to disrupt the duplex enough to "unfold" the hairpin.

Alternatively, the hairpin structure may be unfolded by out-competing the double stranded element of the hairpin structure with "anti-blocking" oligonucleotides. For instance, in the presence of a high concentration of an anti-blocking oligonucleotide that is complementary to one of the strands of the hairpin structure, the interaction (hybridization) between the anti-blocking oligonucleotide and the nucleic acid probe will be favoured over the hairpin structure.

Preferably, however, the hairpin is opened by cleaving the probe.

"Cleavage" is defined broadly herein to include any means of breaking or disrupting a nucleotide chain (i.e. a nucleotide sequence). Cleavage may thus involve breaking a covalent bond. Typically cleavage will involve cleavage of nucleotide chain (i.e. strand cleavage or strand scission), for example by cleavage of a phosphodiester bond.

For instance, the hairpin structure may comprise or may be engineered or modified to comprise a restriction endonuclease recognition sequence. In a preferred embodiment, e.g. where the hairpin structure comprises a restriction endonuclease recognition site, the restriction endonuclease will cleave only a single strand of the duplex portion of the hairpin structure. For example, this may be achieved by hybridising an oligonucleotide (termed herein a "restriction oligonucleotide") to the single-stranded loop of the hairpin structure to comprise a duplex within the loop. At least part of the formed duplex will comprise a restriction endonuclease recognition site, which can be cleaved resulting in unfolding of the hairpin structure. Any suitable restriction endonuclease may be used to unfold the hairpin structure.

In some embodiments, the loop of the hairpin structure may comprise a region of intramolecular complementarity such that it is able to form a duplex within the loop, i.e. the loop contains a double stranded region (a duplex) that forms a protrusion from the loop and is therefore distinct from the "stem" of the hairpin structure. The internal duplex of the loop may comprise a cleavage site, e.g. a restriction endonuclease recognition site, wherein cleavage of the duplex within the loop results in unfolding of the hairpin structure.

Thus, in some embodiments, the additional sequence provided at the end of the first binding site may contain a region of intramolecular complementarity.

In yet further embodiments of the invention an exonuclease enzyme may be used to degrade one strand of the hairpin duplex, thereby releasing the single-stranded loop of the hairpin, i.e. unfolding the probe. The exonuclease enzyme may have 5' or 3' exonuclease activity depending on the orientation of the hairpin structure.

In other embodiments, cleavage may comprise breaking covalent bonds within one or more nucleotides in a nucleic acid sequence. For example, where the hairpin structure comprises uracil residues, at least a portion of the duplex in the hairpin structure may be disrupted by removing one or more uracil bases, i.e. cleavage of said bases from the nucleic acid using a uracil-DNA glycosylase enzyme. Removal of said one or more uracil bases results in the loss of some hydrogen bonds between the two strands of the hairpin duplex, resulting in a loss of stability and unfolding of the nucleic acid domain.

In some embodiments a cleavage site may be created by incorporating one or more uracil residues into the loop sequence. In a particularly preferred embodiment, the hairpin structure can be unfolded by treatment with a uracil-DNA glycosylase (UNG) enzyme in combination with an endonuclease enzyme capable of recognising apurinic/apyrimidinic (AP) sites of dsDNA, e.g. endonuclease IV.

In a further preferred embodiment the hairpin structure may be cleaved, and thereby unfolded, using a nickase enzyme, which cleaves only one strand in the duplex of the hairpin structure. Nickases are endonucleases which cleave only a single strand of a DNA duplex. As described above, a cleavage site may be introduced in the single-stranded loop of the hairpin structure, e.g. by annealing (hybridising) and oligonucleotide to said loop.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is herein incorporated by reference in its entirety and any suitable nickase may be used in the methods of the invention.

In some preferred embodiments that utilise a nickase enzyme, the nickase enzyme is removed from the assay or inactivated following unfolding of the nucleic acid probe to prevent unwanted cleavage of ligation products.

As discussed above, the nucleic acid probe for use in the methods of the invention comprises four target binding sites which are complementary to the regions of the target nucleic acid molecule flanking the target ROI. "Complementarity" as used herein refers to functional complementarity, i.e. capable of mediating hybridisation, and need not refer to 100% complementarity between two nucleic acid molecules. Hybridisation according the present invention includes the formation of a duplex between nucleotide sequences which are sufficiently complementary to each other, whether by Watson-Crick type base pairing or by any analogous base pairing. The hybridisation is a productive hybridisation, that is a hybridisation which is stable enough or strong enough for the probe to be able to perform its function, e.g. for probe/target molecule hybrid to be separated from the sample, or for the cleavage sites created to be cleaved, and for the target fragment to be able to be circularised by ligation.

Thus, complementary nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

It would be a matter of routine to the person skilled in this art appropriately to design the target binding sites in the probe, e.g. taking into account length of the sites, G/C content and Tm etc., and the desired hybridisation pattern (i.e. which of binding sites 2 or 3 hybridises initially to the probe). Typically the target binding site is at least 5 nucleotides long, more typically at least 6, 7, 8, 9, 10, 11, 12, 13, 14, 15, 16, 17, 18, 19, 20, 30, 40 or 50 nucleotides in length or any integer between or up to or above any of these.

The cleavage in step (c) of the method may be achieved by any convenient means but is preferably enzymatic cleavage.

Thus, in a preferred embodiment, the cleavage sites created in the partially double-stranded probe/target molecule hybrid represent a cleavage recognition site, e.g. a sequence that is recognised by one or more enzymes capable of cleaving nucleic acid molecules. The two cleavage sites created in step (c) may either be the same or different.

Any suitable cleavage enzyme may be used to cleave the partially double-stranded construct to release a target fragment comprising the region of interest flanked by the first and second inner flanking sequences which are complementary to the third and second binding regions of the nucleic acid probe, one of which is hybridised to its complementary binding site in the cleaved probe.

Figure 7:
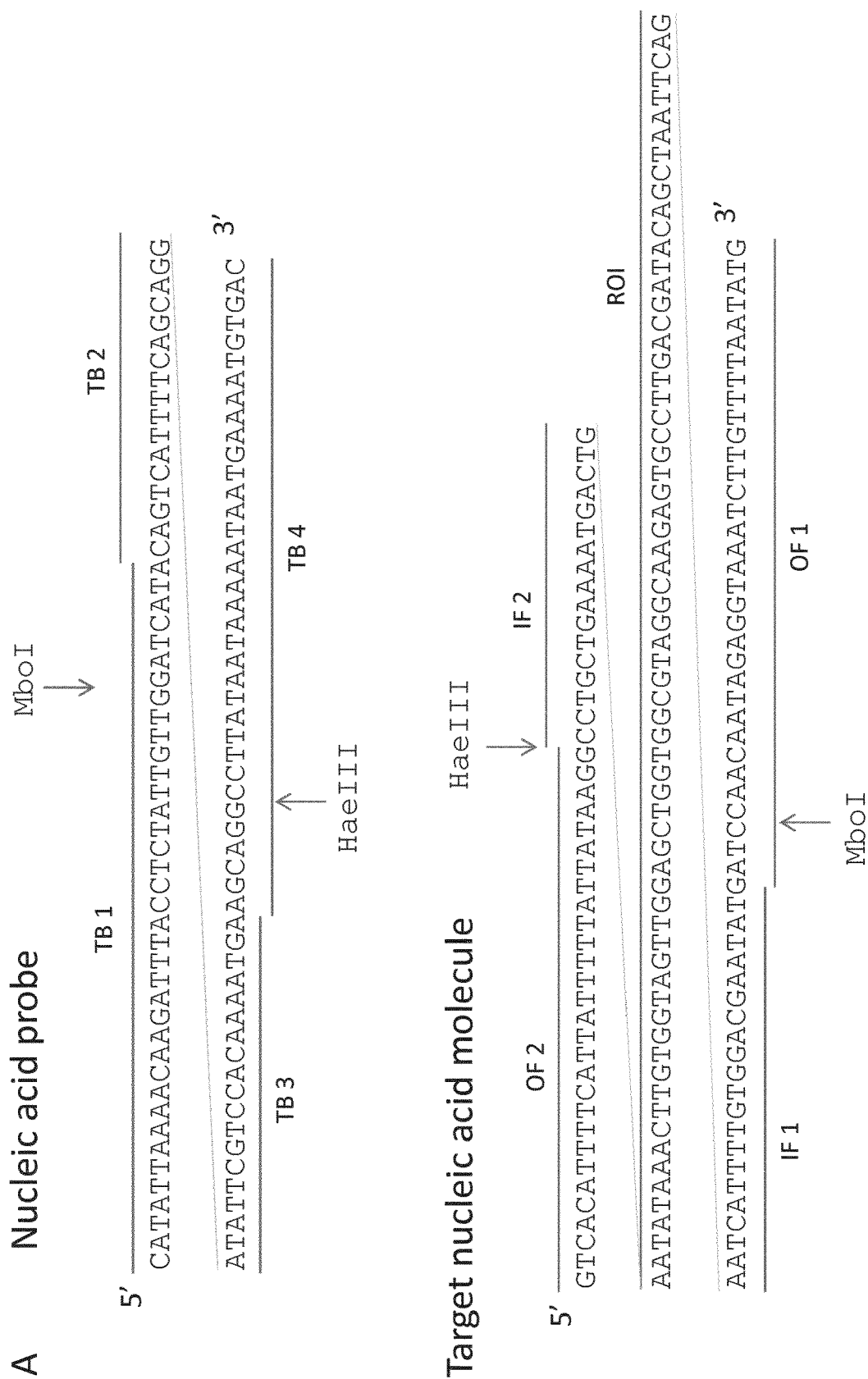
Figure 7:
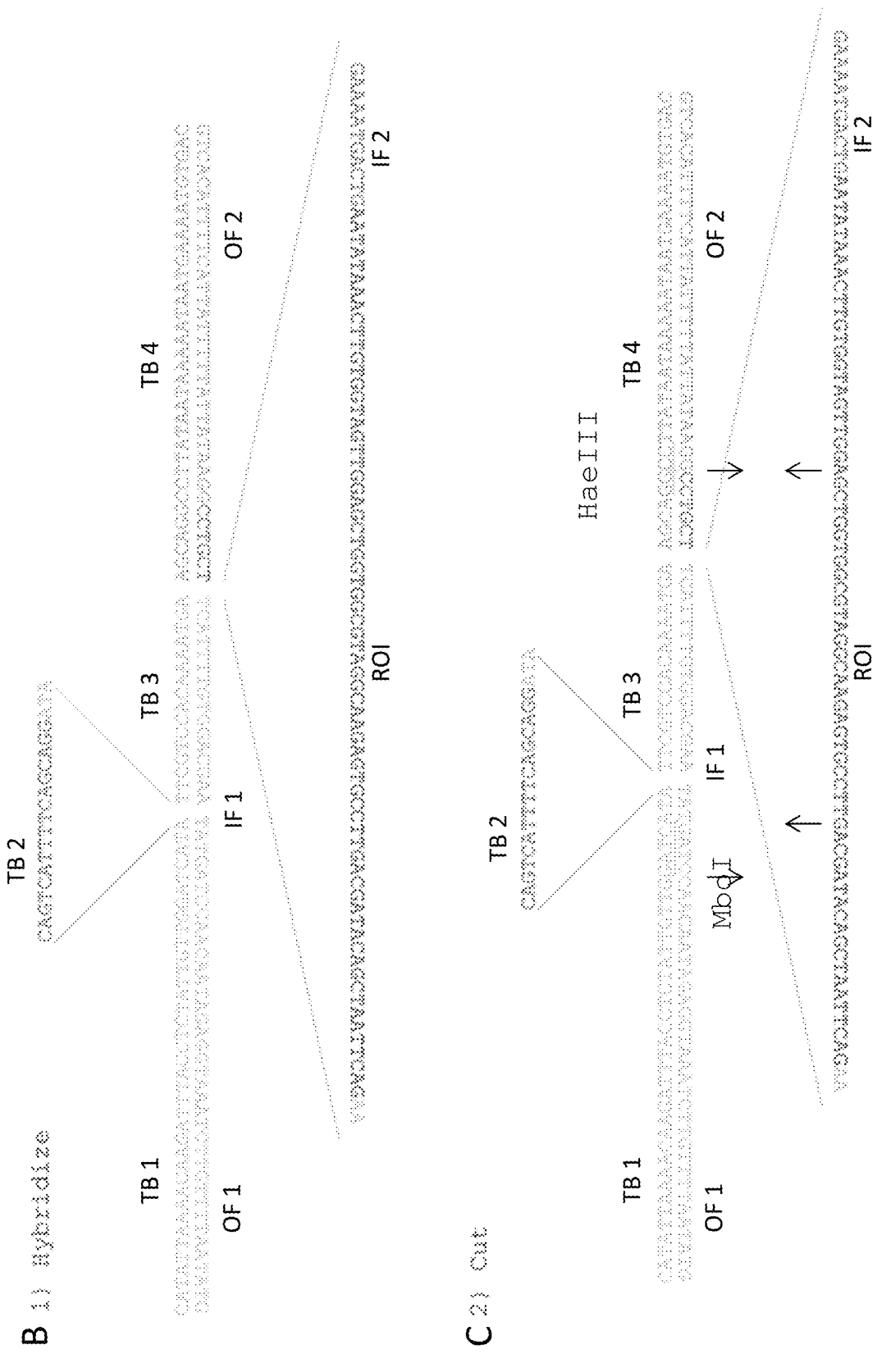
Figure 7:
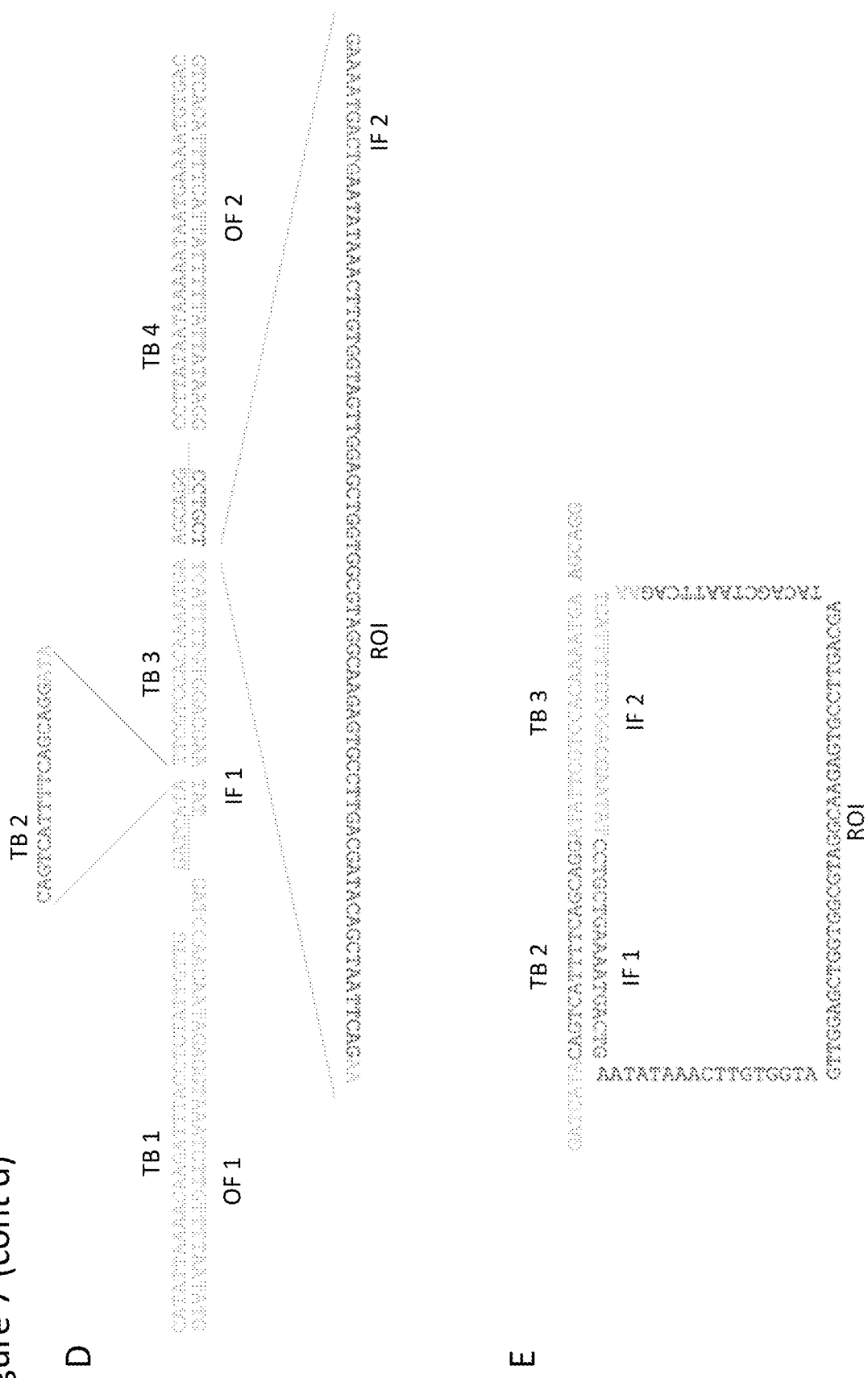

In a preferred embodiment, the cleavage site is a restriction site. In this preferred embodiment the restriction endonuclease will cleave both strands of the cleavage site. The endonuclease may alternatively cleave a single strand, namely the target strand. By way of example, FIG. 7 shows a representative probe and target molecule showing how a cleavage site may be created and cleaved.

As discussed above, the second and third target binding sites template the ligation and thereby circularisation of the target fragment, whereby the second or third target binding site that is not hybridised to the target nucleic acid molecule may hybridise to its complementary region flanking the target ROI, thereby to bring the ends of the target fragment into juxtaposition for ligation.

As discussed above, the ends of the target fragment may be positioned directly adjacent to each other where the second and third target binding sites are directly adjacent within the probe, and thus ligation may take place directly between the ends of the target fragment. Alternatively, the ends of the target fragment may not be positioned directly adjacent to each other, i.e. where there is an intervening sequence between the second and third target binding sites in the probe. In such instances, the ends of the target nucleic acid molecule probe may be ligated indirectly, e.g. via one or more gap oligonucleotides or after the "gap-fill" extension of the 3' end of the oligonucleotide. The gap oligonucleotide will be complementary to the intervening sequence between the second and third target binding sites, and may either be added to the sample separately to the probe, or may be hybridised to the nucleic acid probe prior to the selection of the target ROI.

The ligation step may be performed by procedures well known in the art. Enzymes appropriate for the ligation step are known in the art and include, e.g. Tth DNA ligase, Taq DNA ligase, *Thermococcus* sp. (strain 9°N) DNA ligase (9°N™ DNA ligase, New England Biolabs), Ampligase™ (Epicentre Biotechnologies) and T4 DNA ligase.

A target ROI circularised according to the method herein may be directly separated, analysed or detected, or may instead first be amplified. Indeed it may be detected by means of the amplification. Amplification of the target ROI may be performed by any suitable method for amplifying nucleic acids and in particular circular nucleic acids. Amplification may be linear or exponential, as desired, where representative amplification protocols of interest include, but are not limited to: polymerase chain reaction (PCR); isothermal amplification, rolling-circle amplification (RCA), and their well-known variants, such as hyperbranched RCA, etc. Other nucleic acid amplification methods may include Loop mediated isothermal amplification (LAMP), SMart Amplification Process (SMAP), Nucleic acid sequence based amplification (NASBA), or ligase chain reaction (LCR). Where the detection step includes an amplification, the amplification product may be detected, to detect the target ROI.

Amplification methods based on RCA represent one preferred embodiment and in a particular aspect the amplification may involve a second round of RCA, for example a superRCA (sRCA) reaction as described in WO2014/076209, herein incorporated by reference. In such a sRCA reaction a secondary RCA reaction is performed using a further RCA template circle and the RCA is primed by a primer which is hybridised to the primary RCA product (here the amplicon of a first RCA step using the circularised target fragment as template). The primer is provided in such a way that it remains hybridised to the first RCA product throughout the secondary RCA, such that the secondary RCA product is localised to the primary RCA product. In a further preferred embodiment of a localised super RCA reaction, the secondary RCA reaction may be templated by a padlock probe which hybridises to the primary RCA product and is ligated to form a circle which is then subjected to a secondary RCA reaction (a so-called "Padlock sRCA" which is described in our co-pending GB patent application No. 1320145.4, published as WO2015/071445).

In such sRCA reactions the secondary RCA product is unrelated to the primary RCA template, i.e. the first circle, which in this case is the circularised target fragment. Thus a sRCA is used as a means of signal amplification, e.g. in a detection method, rather than as means of amplifying the target ROI in, e.g. a preparative method. For such purposes, a circle-to-circle RCA reaction (as described in WO/2003/012119) may be used to enhance the amount of product generated by the RCA, which is essentially a linear amplification process, or a hyperbranched RCA.

Alternatively an exponential amplification reaction such as PCR may be used. Amplification of the circularised target fragment by PCR represents another preferred embodiment. As discussed above, binding sites for PCR primers may conveniently be provided by a gap oligonucleotide incorporated into the circularised molecule. Alternatively, amplification primers may be designed to bind elsewhere in the target fragment. In multiplex embodiments universal or common PCR primer binding sites may be introduced and used to amplify different circularised target fragments in parallel using a single primer pair. Such use of a single primer pair has been demonstrated in other contexts and applications, e.g. for Selector probes as disclosed in U.S. Pat. No. 7,883,849 as discussed above.

It will be apparent that the portions of the probe that template the ligation of the target ROI (i.e. the second and third target nucleic acid binding sites) can remain bound to the target ROI after ligation and circularisation have taken place. Thus in one embodiment of the present invention, the second or third target binding site of the nucleic acid probe (depending on the orientation) may act as a primer to initiate rolling circle amplification. In an alternative embodiment, a primer may be added to the sample to initiate rolling circle amplification.

Although amplification of the circularised target fragment is convenient and in many applications of the method it may be preferred, it is possible also to separate the circularised target fragment in other ways, for example by digesting any linear molecules present using an exonuclease, thereby to enrich for circular nucleic acids, or by other nucleic acid separation or fractionation procedures known in the art.

Figure 5:
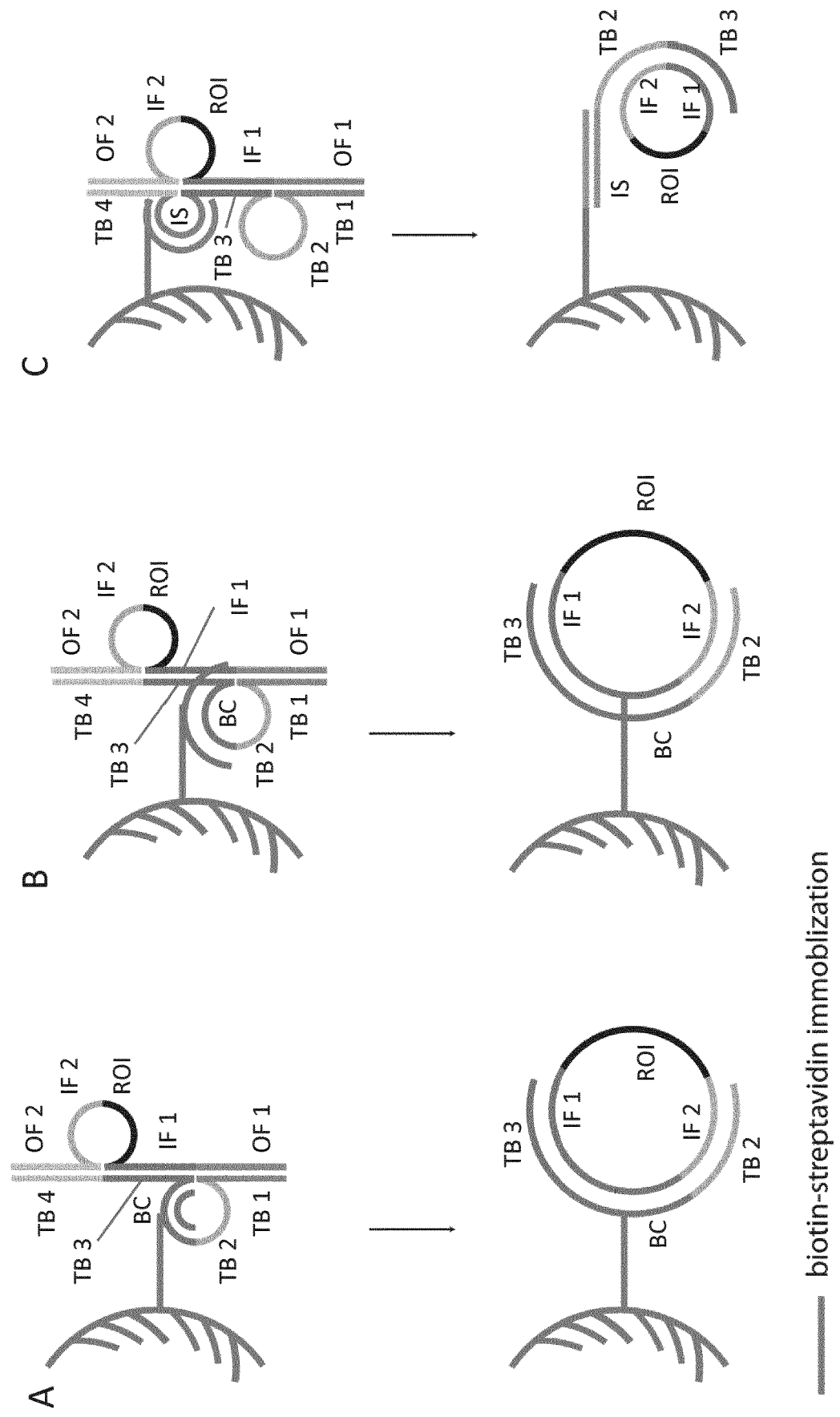

It is further apparent that the method outlined above can be used to generate a circularised molecule comprising the target ROI in solution. Thus the method may be performed in a homogenous format. However in an alternative embodiment the probe may be immobilised on a solid support prior to, or after, hybridisation to the target nucleic acid molecule, or indeed at any stage of the method. Means for immobilising the probe or target fragment may be introduced by way of an intervening sequence between any two of its target binding sites. Such a method is depicted in FIG. 5.

As shown, the intervening sequence may be between the second and third target binding sites, and may be hybridised to a complementary nucleic acid molecule, thereby forming a partially double-stranded nucleic acid probe. In a first embodiment the intervening sequence may be attached to a solid support. In a second embodiment the complementary nucleic acid molecule can be attached to a solid support. In a further embodiment, the intervening sequence may be between the first and second, or between the third and fourth target binding sites, and may be hybridised to a complementary nucleic acid molecule, thereby forming a partially double-stranded nucleic acid probe, and the complementary nucleic acid molecule can be attached to a solid support.

The circularised target fragment which is selected according to the method of the invention, or an amplicon thereof, may be detected. The detection may be by nucleic acid readout platform, including sequencing or any sequence-analysis procedure, real-time PCR and sRCA. A selected and amplified target ROI can be detected or analysed using a number of known means, e.g. by hybridisation of a detection probe to the amplified product which may be labelled, or which may take part in further signal-giving or signal-amplification reaction, e.g. a ligation-based reaction, e.g. a padlock probe, or a probe for an OLA assay. Padlock probes may be detected in further amplification reactions, e.g. in a sRCA reaction.

Thus the amplified products of an amplification reaction may be detected using any convenient protocol, which may detect the amplification products non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the amplification product, as opposed to double stranded molecules in general, may be employed to detect the amplification. In these embodiments, the signal producing system may include a detection probe that specifically binds to a sequence found in the amplification product, where the detection probe may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probes include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled detection probes are labelled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others' electronic structure. If the fluorescence-modifying group is a quenching group, this will result in the quenching group preventing the fluorescent group from even emitting light.

The energy transfer labelled detection probe, e.g. oligonucleotide, may be structured in a variety of different ways, so long as it includes a donor, acceptor and target nucleic acid binding domains. As such, the energy transfer labelled oligonucleotides employed in these embodiments of the method are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector. The acceptor domain includes the fluorescence energy acceptor. The acceptor may be positioned anywhere in the acceptor domain, but is typically present at the 3' terminus of the nucleic acid detector or probe.

In addition to the fluorophore and acceptor domains, the energy transfer labelled probe oligonucleotides also include a target nucleic acid binding domain, which binds to a target nucleic acid sequence (e.g. a tag, for example a barcode sequence) found in the amplification product of interest (as described above). Specific examples of such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Examples of other types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes.

The next step in the subject methods is signal detection from the labelled amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target ROI. Depending on the particular label employed, detection of a signal may indicate the presence or absence of the target ROI.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or where the sample is a tissue sample on a microscope slide, fluorescence may be detected using a fluorescence microscope. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time. Thus, in some embodiments multiple targets may be detected in parallel, whereas in other embodiments multiple targets may be detected sequentially.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analysed, for example by calculating the area under the melting peaks and these data plotted against the number of cycles.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the detection probe and the target sequence or degradation of the detection probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target present in the sample, e.g., as correlated to the amount of amplification product detected in the reaction mixture, suggestive of the fact that the amplification reaction has proceeded and therefore the target was in fact present in the initial sample. Quantification is also possible by monitoring the amplification reaction throughout the amplification process. Quantification may also include assaying for one or more nucleic acid controls in the reaction mixture, as described above.

The method of the invention may have a number of uses and applications. One such use may be the preparation of substrates or templates for sequencing or other sequence analysis, such as determining the methylation status of a target ROI. As discussed above, the method may also be used for detection, e.g. for identification of a target ROI or for detection of the presence or absence, or amount or level, of a particular target ROI in a given sample. Thus the method may be used for the detection of a target organism, e.g. a pathogen in a sample, which may be useful clinically or for research or other purposes, e.g. epidemiological studies or for studying microbial resistance etc. Further the method may find utility in screening for or detecting rare mutations, e.g. when screening for minimal residual disease in cancer, particular when combined with sensitive detection strategies such as sRCA.

As discussed above, the method of the invention has a number of advantages, including for use in such applications, for example a much reduced sequence error rate. A further advantage is that it does not require the correct 5' and 3' ends of a probe to be present in order for selection to take place. N-1 and N-2 deletions are commonly present in synthesised nucleic acids, particularly when longer oligonucleotides are used. For circularisation it is also required that the 5' end of the oligonucleotide to be circularised is phosphorylated. 5' phosphorylation of probes is a technical hurdle and expensive if large numbers of probes are used. Synthesised nucleic acid probes can often lack a phosphate group at their 5' end, which can prevent ligation and circularisation of a target nucleic acid molecule once it has been selected, for example in the context of a Selector probe. The present invention therefore bypasses both of these obstacles to the selection of target nucleic acid sequences, reducing the cost associated with ensuring that highly homogeneous phosphorylated nucleic acid probes are used.

Advantageously, the present invention can as mentioned above be in homogenous (non solid phase) or in solid phase-based formats. A selected target nucleic acid can therefore be identified either in situ or in an array-based assay using any one of a number of techniques known in the art. Use of a solid phase may enable or facilitate washing steps to be included.

Since, as mentioned above, the original target molecule is captured in the circularised target fragment, and not an amplicon or copy thereof, the method permits methylation status to be investigated. Suitable methods for the analysis of methylation patterns are well known in the art and may include, e.g. mass spectrometry, Methylation-Specific PCR (MSP), bisulfite sequencing (BS-Seq), the HELP assay, DNA microarrays (MeDIP-chip), High Resolution Melt Analysis (HRMA) etc.

The probes, and optionally other components for performing the method of the invention may conveniently be provided in kit form.

Accordingly, in a further aspect the invention provides a kit, more particularly a kit for selecting a target ROI in a target nucleic acid molecule, said kit comprising:

(a) a probe of the invention as hereinbefore defined; and optionally one or more further components selected from:

(b) means for cleaving the cleavage sites created by hybridisation of the probe, e.g. one or more restriction enzymes;

(c) means for unfolding a hairpin structure in the probe, e.g. one or more cleavage enzymes as discussed above;

(d) a ligase enzyme;

(e) one or more gap oligonucleotides;

(f) means for amplification of the circularised target fragment, e.g. one or more amplification primers, (e.g. PCR primers) and/or amplification enzymes (e.g. a polymerase, for example phi29 or another strand displacing polymerase for RCA, or a polymerase suitable for PCR, as known in the art);

(g) means for detecting the circularised target fragment or an amplicon thereof, e.g. one or more detection probes, or labels, or means for a further detection reaction, e.g. means for performing a sRCA reaction, for example a primer for the sRCA reaction, a template for the sRCA reaction or a padlock probe etc., as described above.

The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, flash drive, etc., on which the information has been recorded. Yet another means that may be present is a website address which may be used via the internet to access the information at a removed site. Any convenient means may be present in the kits.

The invention will be further described in the following non-limiting Examples with reference to the drawings in which:

FIG. 1 illustrates a probe according to the invention and indicates the arrangement of the target binding sites in the probe and the sequences in the target nucleic acid molecule flanking the target region of interest.

FIG. 2 indicates alternative target probes of the present invention comprising further elements in addition to the target binding sites. A) Probe with intervening sequences between the first and second, and third and fourth target binding sites; B) Probe with an intervening sequence between the second and third target binding site and which includes a universal tag sequence, hybridised to gap oligonucleotide that can act as a circularisation cassette for ligation; C) Probe with intervening sequences between the first and second, second and third, and third and fourth target binding sites. The intervening sequences between the first and second, and the third and fourth target binding sites may comprise capture elements; D) Probe with an intervening sequence between the second and third target binding site, hybridised to a partially complementary sequence further comprising a sample-specific identificatory sequence (Sample ID); E) Probe with an intervening sequence between the second and third target binding sites, and with an additional sequence beyond the first target binding site. These sequences can hybridise to form a hairpin structure that can be unfolded by cleavage adjacent to the first target binding site.

FIG. 3 illustrates the selection method described herein. Probes and genomic DNA are mixed and undergo denaturation, to allow the hybridisation of three of the target binding sites in the nucleic acid probe to the target nucleic acid molecule. Next restriction enzymes cleave the partially double-stranded nucleic acid molecule to release a target fragment comprising the target ROI flanked by the first and second inner flanking sequences. The ends of the target fragment are then ligated, templated by the second and third target binding sites.

FIG. 4 indicates the selection method when a nucleic acid probes contains an intervening tag sequence comprising a barcode between the second and third target binding sites. The target fragment is circularised using an additional circularisation cassette (a gap oligonucleotide), complementary to the intervening sequences.

FIG. 5 indicates ways that a probe can be immobilised on a solid support. A) A probe with an intervening sequence between the second and third target binding sites can be immobilised directly on a solid support, and a circularisation cassette (gap oligonucleotide) complementary to the intervening sequence is used to aid circularisation. B) A probe can be immobilised via a sequence complementary to an intervening sequence between the second and third target binding sites. C) A probe can be immobilised via a sequence complementary to an intervening sequence between either the first and second, or third and fourth target binding sites.

FIG. 6 indicates how a target ROI can be detected in situ in genomic DNA, and RCA products visualised via hybridisation of fluorescently labelled oligonucleotides.

FIG. 7 shows a representative probe for use in the method disclosed herein, and illustrates how a nucleic acid probe and target nucleic acid molecule interact during the various stages of the selection method. A) The probe comprises four target binding sites (labelled TB 1-4), and target binding sites 1 and 4 contain sequences capable of creating MboI and HaeIII restriction enzyme recognition sites when hybridised to the target molecule. The target nucleic acid molecule comprises a target region of interest flanked by first and second inner and outer flanking sequences. B) The probe and target molecule interact to form a partially double-stranded nucleic acid construct. C) Restriction enzyme digestion of the partially double-stranded construct at the MboI and HaeIII sites. D) Releasing target nucleic acid fragment comprising the target ROI flanked by the first and second inner flanking sequences. E) Circularisation of the target fragment templated by the second and third target binding sites of the probe.

Figure 8:
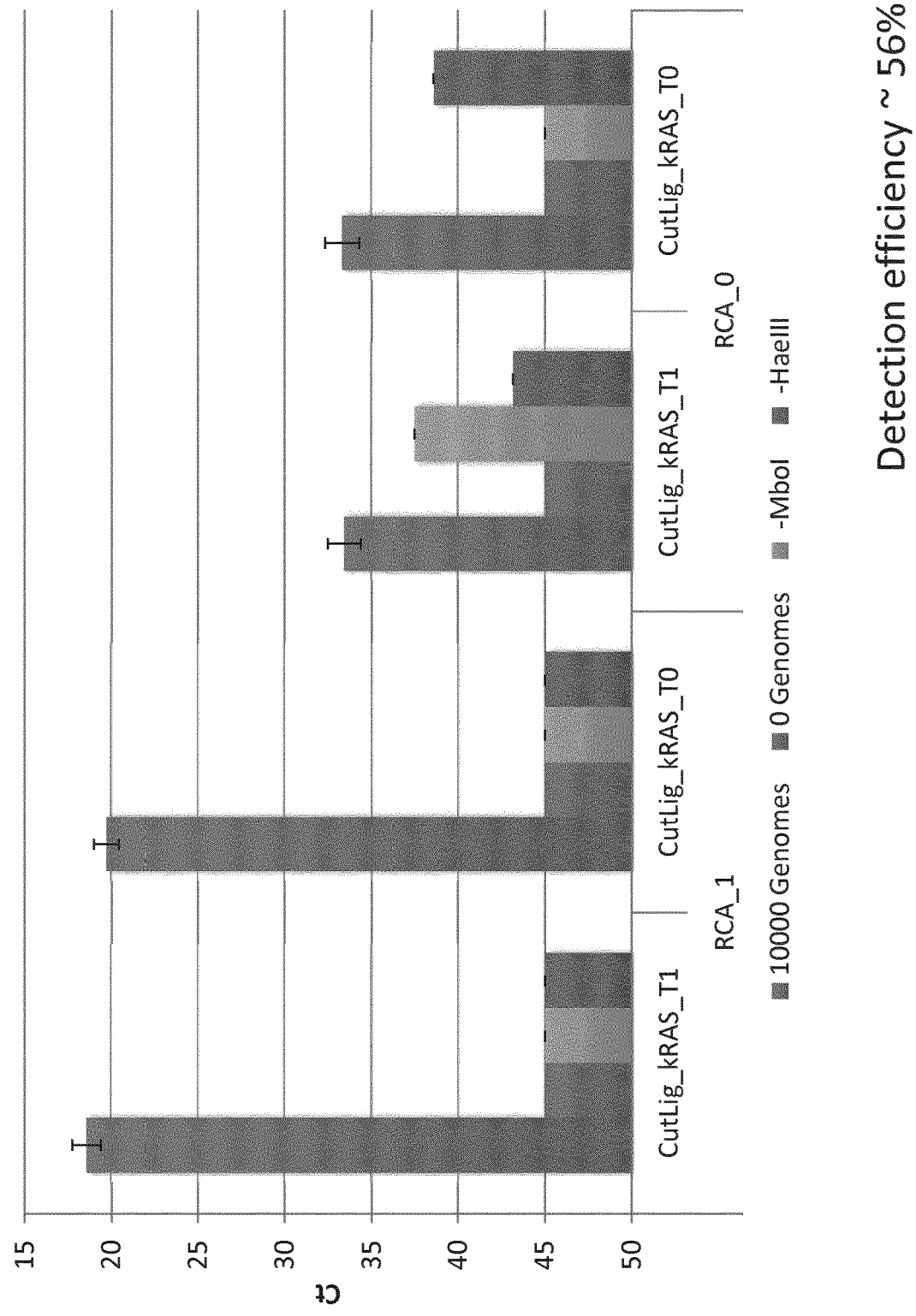

FIG. 8 shows the results of capturing the KRAS target ROI from Example 4 using KRAS nucleic acid probes with (T1) and without (T0) poly-T intervening sequences. The selection method was performed in the presence and absence of genomic DNA, ModI and HaeIII. Signal amplification by RCA (RCA 1) was also performed, compared to a control sample (RCA_0).

Figure 9:
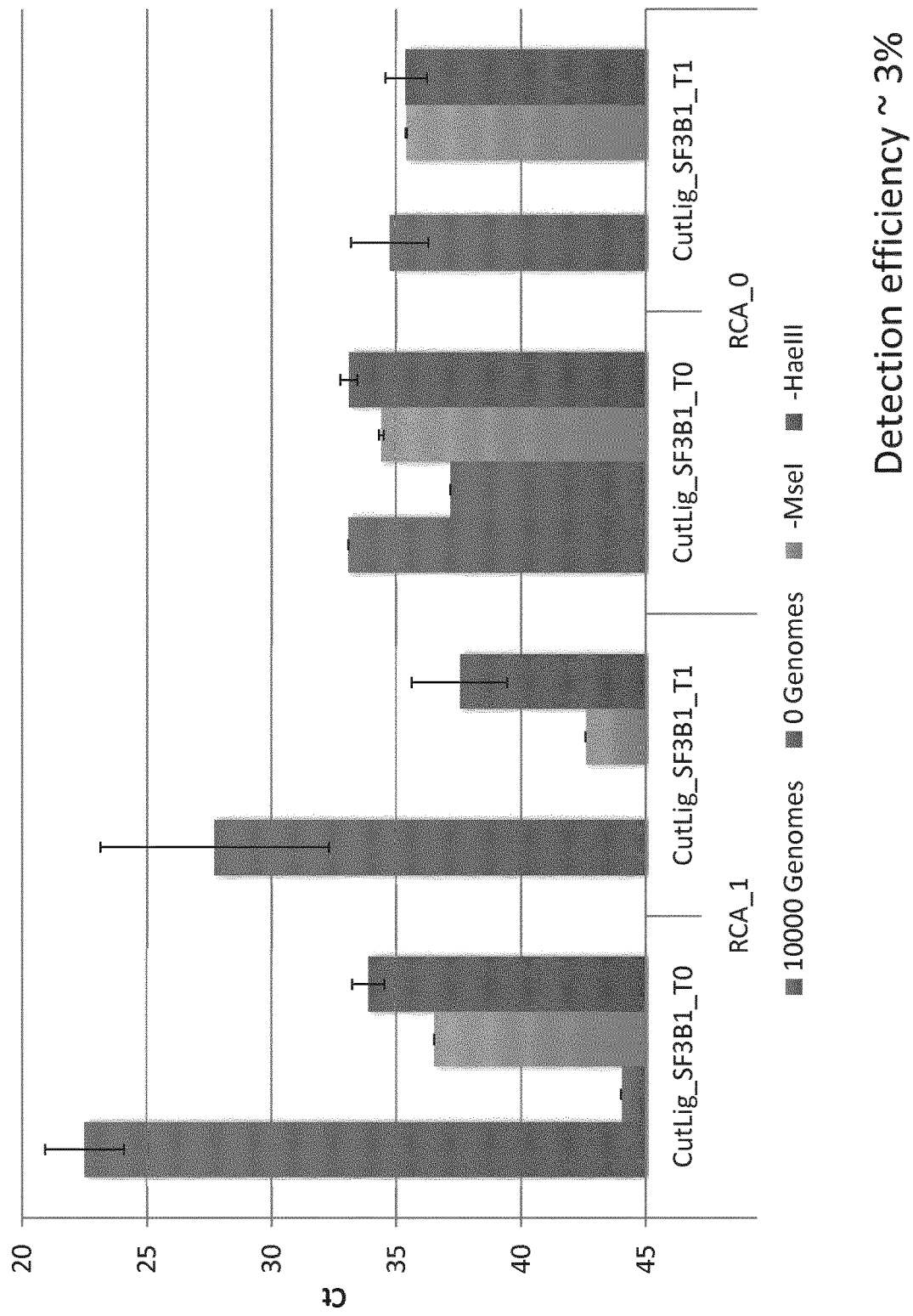

FIG. 9 shows the results of capturing the SF3B1 target ROI from Example 4 using SF3B1 nucleic acid probes with (T1) and without (T0) poly-T intervening sequences. The selection method was performed in the presence and absence of genomic DNA, MseI and HaeIII. Signal amplification by RCA (RCA 1) was also performed, compared to a control sample (RCA_0).

Figure 10:
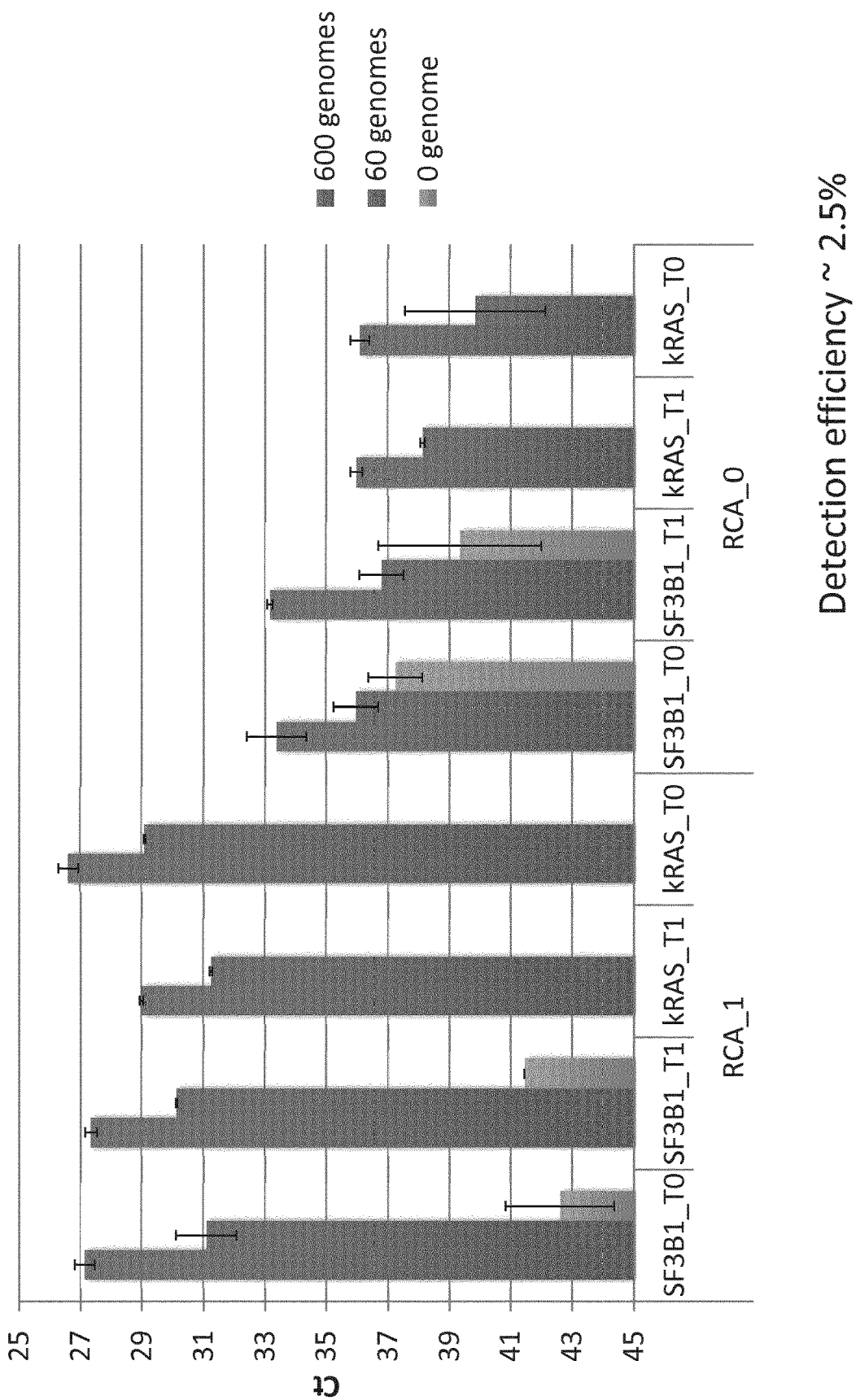

FIG. 10 indicates the sensitivity of the selection method of the present invention. 600, 60 and 0 copies of genomic DNA were used and the target ROIs from Example 4 were detected using their respective probes. Signal amplification by RCA (RCA_1) was also performed, compared to a control sample (RCA_0).

Figure 11:
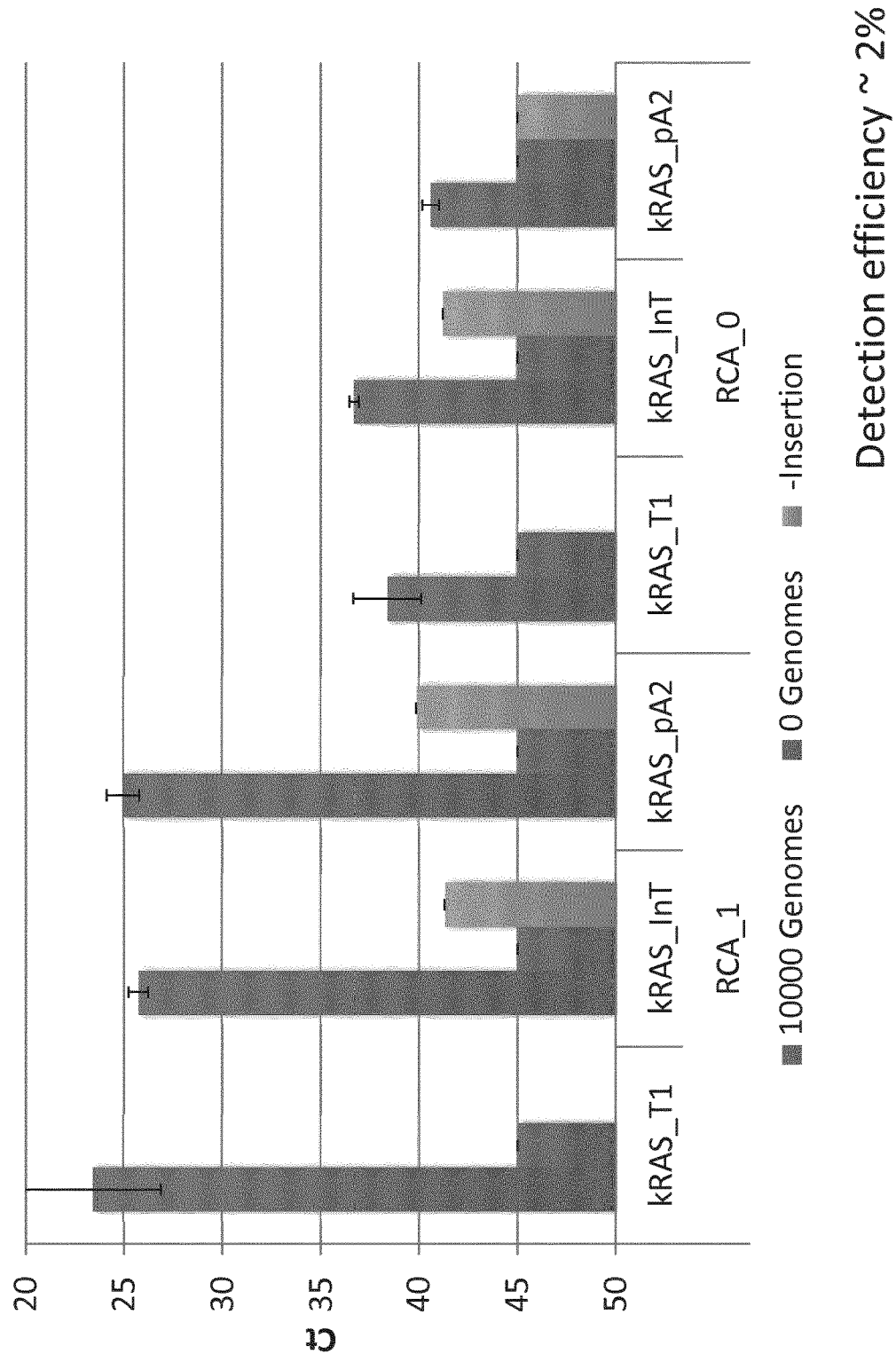

FIG. 11 shows the results of selecting the KRAS target region of interest from Example 4 using probes with a barcode sequence between the second and third target binding sites. The KRAS_T1, KRAS_InT and KRAS_A2 probes were used to select the KRAS target ROI. The selection method was performed in the presence and absence of genomic DNA. Signal amplification by RCA (RCA_1) was also performed, compared to a control sample (RCA_0).

Figure 12:
Figure 12:
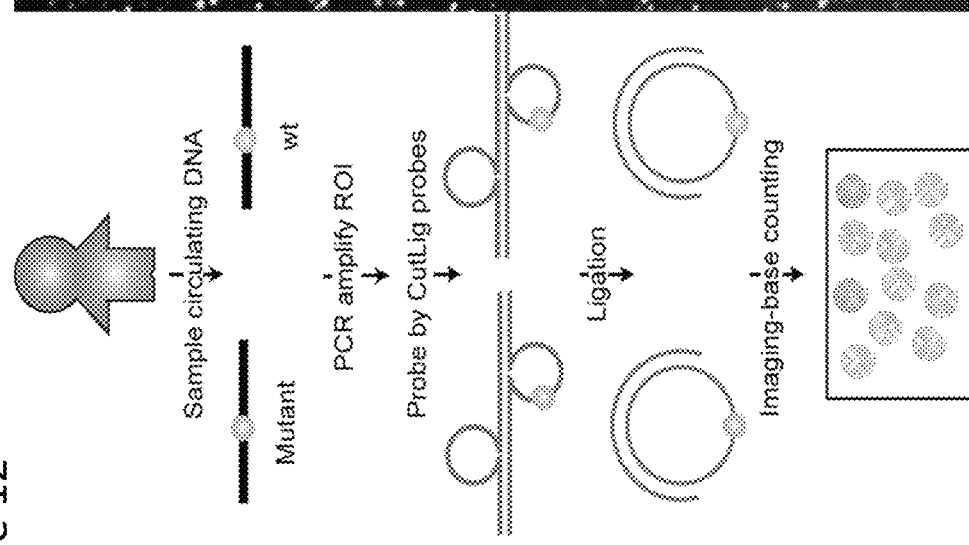

FIG. 12 indicates that the present method can be used to detect mutations within a target ROI. Target sequences were detected using oligonucleotides labelled with Cy3 and Cy5. Mutant sequences were detected in approximately 50% abundance in the left hand panel, and a selection of detected amplification products for the mutant sequence are highlighted with arrows.

Figure 13:
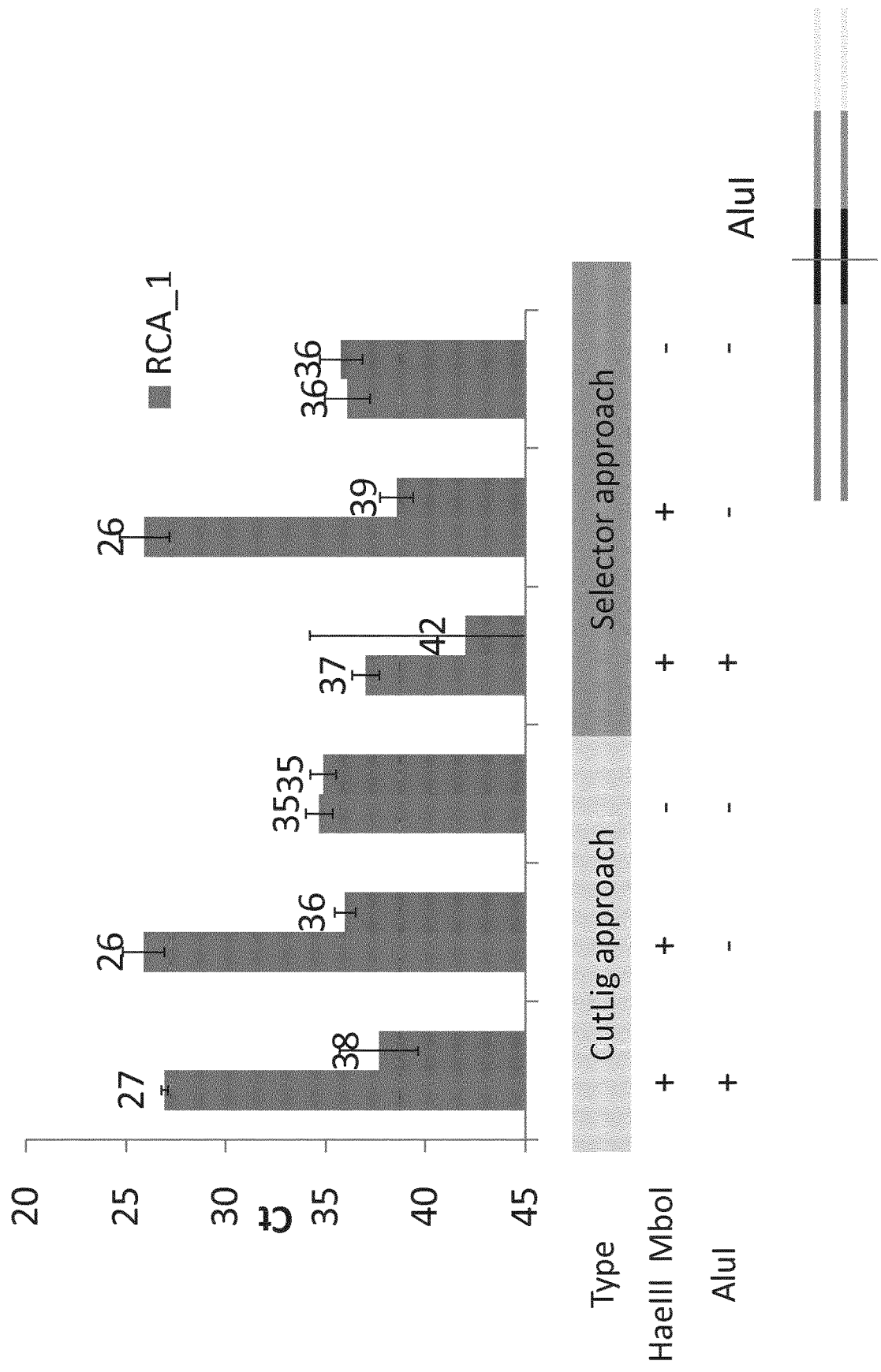

FIG. 13 demonstrates that unwanted target-digestion is reduced for the probes of the present invention, compared with conventional double-stranded selector probes. Loss of signal is only seen when AluI (which cuts double stranded ROI only) is added to the cutting mix in the selector method, but not the method of the present invention.

EXAMPLES

The Examples demonstrate the method of the present invention and describe the process of developing probes suitable for selecting sequences from a target nucleic acid molecule. The selection method is shown to result in the target-specific amplification of a nucleic acid product, and a number of different nucleic acid probes are shown to work in the method of the invention.

Example 1—Exemplary Nucleic Acid Sequence for the Detection of a Target of Interest A KRAS genomic fragment can be detected by the methods of the present invention. The sequence of a genomic fragment that can be detected by the method described herein, and the sequence of a nucleic acid probe used its detection are shown below. The regions of the nucleic acid probe corresponding to the four target binding sites, and the regions of the target nucleic acid molecule corresponding to the flanking sequence and region of interest are shown in FIG. 7A.

The KRAS genomic fragment (SEQ ID NO:1) has the following sequence (5' 4 3'), the target region of interest is shown in bold:

GTCACATTTTCATTATTTTTATTATAAGGCCTGCTGAAAATGACTGAATA

TAAACTTGTGGTAGTTGGAGCTGGTGGCGTAGGCAAGAGTGCCTTGACGA

TACAGCTAATTCAGAATCATTTTGTGGACGAATATGATCCAACAATAGAG

GTAAATCTTGTTTTAATATG

The nucleic acid probe (SEQ ID NO:2) used to detect the KRAS genomic fragment (KRAS_T0) has the following sequence (5'→3'):

CATATTAAAACAAGATTTACCTCTATTGTTGGATCATACAGTCATTTTCA

GCAGGATATTCGTCCACAAAATGAAGCAGGCCTTATAATAAAAATAATGA

AAATGTGAC

The interaction between the target binding sites of the nucleic acid probe and their respective regions of complementarity in the target nucleic acid molecule is shown in FIG. 7B. FIGS. 7C-7E indicate the progression of the method of the present invention, which is carried out as shown in FIG. 3. Restriction enzymes MboI and HaeIII are used to release the target fragment.

Example 2—Genomic Fragment Capture and Amplification by Nucleic Acid Probes

Approximately 1e4 human male genomes (Promega) and 12.5 nM nucleic acid probes were mixed in 20 µl 0.5×PBS and heated at 95° C. for 20 min, followed by immediate chill on ice. 5 µl cutting and ligation mix were added to the target and probe mix reaching final concentrations of 1× CutSmart buffer (NEB), 0.02 U/µl of each restriction enzymes (HaeIII (New England Biolabs (NEB)) and MboI (NEB) for KRAS probes, HaeIII and MseI (NEB) for SF3B1 probes), 0.5 mM NAD (Sigma-Aldrich) and 0.02 U/µl ampligase (Epicentre biotechnology). The mix was incubated at 37° C. for 30 min and 55° C. for 15 min. One µl of RCA mix was added to 10 µl of ligation products reaching final concentrations of 0.23 µg/µl BSA (NEB), 0.57 mM d(A, T, G, C)TP (Thermo Scientific) and 0.05 U/µl phi29 DNA polymerase (Thermo Scientific). The reaction was carried out at 37° C. for 60 min and 65° C. for 15 min. For real-time PCR readout, 40 µl PCR mix were added to RCA products reaching final concentrations of 0.8×PCR buffer (Invitrogen), 2.5 mM MgCl$_2$ (Invitrogen), 100 nM of primer pairs (shown in Table 2), 0.5× SYBR (Molecular probes), 0.06 U/µl platinum Taq DNA polymerase (Invitrogen), 0.2 mM d(A, U, G, C)TP (Thermo Scientific), 0.002 U/µl UNG (Thermo Scientific). Real time PCR was carried out in Stratagene MX3005 PCR machine (Agilent Technologies) using a thermal profile with an initiation at 95° C. for 2 min followed by 45 cycles of 95° C. for 15 sec and 60° C. for 1 min.

TABLE 1

List of probes used to detect target nucleic acid regions of interest.

| SEQ ID NO: | Probe name | Probe target | Probe sequence |
|---|---|---|---|
| 2 | kRAS_T0 | KRAS | CATATTAAAACAAGATTTACCTCTATTGTTGGATCATACAGTCATTTTCAGCAGGATATTCGTCCACAAAATGAAGCAGGCCTTATAATAAAAATAATGAAAATGTGAC |
| 3 | kRAS_T1 | KRAS | CATATTAAAACAAGATTTACCTCTATTGTTGGATCATATTTTTTTTTTTTTTTTCAGTCATTTTCAGCAGGATATTCGTCCACAAAATGATTTTTTTTTTTTTTTAGCAGGCCTTATAATAAAAATAATGAAAATGTGAC |
| 4 | KRAS_InT | KRAS | CTATTAAAACAAGATTTACCTCTATTGTTGGATCATATGAATTTCAGCAGGGATACCGGACCAGGTTTCGCCGATTCGAGAACGCAGTGTCATATTCGTCCACAAAATGATGAAAGCAGGCCTTATAATAAAAATAATGAAAATGTGACGACACTGC |
| 5 | kRAS_A2 | KRAS | CTATTAAAACAAGATTTACCTCTATTGTTGGATCATATAAAAAAAAAAAAAAAAAAAAAAAATCAGTCATTTTCAGCAGGGATACCGGACCAGGTTTCGCCGATTCGAGAACGCAGTGTCATATTCGTCCACAAAATGATGAAAGCAGGCCTTATAATAAAAATAATGAAAATGTGACGACACTG |
| 6 | kRAS cassette | | GACACTGCGTTCTCGAATCGGCGAAACCTGGTCCGGTATC |
| 7 | SF3B1_T0 | SF3B1 | GATACCCTTCCATAAAGGCTTTAACACACCAAGGCAGCAATGGACACAGAATCAAAAGATTCGCAATGGCCAAAGCACTGATGGTCCGAA |
| 8 | SF3B1_T1 | SF3B1 | GATACCCTTCCATAAAGGCTTTAACACATTTTTTTTTTTTTTCCAAGGCAGCAATGGACACAGAATCAAAAGATTCGTTTTTTTTTTTTTTTCAATGGCCAAAGCACTGATGGTCCGAA |

TABLE 2

List of PCR primers used to detect amplification products.

| SEQ ID NO: | Primer name | Primer target | Primer sequence |
|---|---|---|---|
| 9 | kRAS_PCR1 | KRAS | CGTGCCTTGACGATACAGCTAA |
| 10 | kRAS_PCR2 | KRAS | CAAGGCACTCTTGCCTACG |
| 11 | SF3B1_PCR1 | SF3B1 | GATTCTGTGTCCATTGCTGC |
| 12 | SF3B1_PCR2 | SF3B1 | GAGTTGCTGCTTCAGCCAAG |

TABLE 3

List of target nucleic acid molecules.

| SEQ ID NO: | Target name | Target sequence |
|---|---|---|
| 1 | kRAS | GTCACATTTTCATTATTTTTATTATAAGGCCTGCTGAAAATGACTGAATATAAACTTGTGGTAGTTGGAGCTGGTGGCGTAGGCAAGAGTGCCTTGACGATACAGCTAATTCAGAATCATTTTGTGGACGAATATGATCCAACAATAGAGGTAAATCTTGTTTTAATATG |
| 13 | SF3B1 | GTCTTGTGGATGAGCAGCAGAAAGTTCGGACCATCAGTGCTTTGGCCATTGCTGCCTTGGCTGAAGCAGCAACTCCTTATGGTATCGAATCTTTTGATTCTGTGTTAAAGCCTTTATGGAAGGGTATCCGCCAACAGAGGAAAG |

The KRAS_T0 and KRAS_T1 nucleic acid probes shown in Table 1 were used to select the target region of interest from the KRAS genomic fragment shown in Table 3. The target region of interest is shown in bold. The KRAS_T1 probe comprised the same target binding sites as the KRAS_T0 probe, but further comprised a poly-T intervening sequence between its first and second, and third and fourth target binding sites.

Positive signals were only seen for the amplification product after PCR amplification when genomic DNA and both the MboI and HaeIII restriction enzymes are present in the reaction sample. Where only one of the restriction enzymes or genomic DNA was not present, near baseline signals were detected. Signals from reactions with RCA amplifications (RCA_1) were ~1000-fold increased compared to reactions with no RCA (RCA_0), indicating successful circularisation of target fragments after enzymatic cleavage. No significant difference was observed for the probes with and without the poly-T intervening sequences. The results of the amplification of the KRAS target region of interest are shown in FIG. 8. A detection efficiency of 56% was estimated for the KRAS_T1 probe, assuming that approximately 1e4 genomes were present in each assay with 40% sampling efficiency throughout the protocol. A 1 hour RCA produces ~1000-fold amplification at 37° C. and Ct 40 corresponds to 1 copy of a DNA amplicon in a PCR reaction. Error bars are the standard deviation for duplicate measurements.

The SF3B1_T0 and SF3B1_T1 nucleic acid probes shown in Table 1 were used to select the target region of interest from the SF3B1 genomic fragment shown in Table 3. The target region of interest is shown in bold. The SF3B1_T1 probe comprised the same target binding sites as the SF3B1_T0 probe, but further comprised a poly-T intervening sequence between its first and second, and third and fourth target binding sites.

Positive signals were only seen for the amplification product after PCR amplification when genomic DNA and both the MseI and HaeIII restriction enzymes are present in the reaction sample. Where only one of the restriction enzymes or genomic DNA was not present, near baseline signals were detected. Signals from reactions with RCA amplifications (RCA_1) were ~1000-fold increased compared to reactions with no RCA (RCA_0), indicating successful circularisation of target fragments after enzymatic cleavage. No significant difference was observed for the probes with and without the poly-T intervening sequences. The results of the amplification of the SF3B1 target region of interest are shown in FIG. 9. A detection efficiency of 3% was estimated for the SF3B1_T1 probe. Error bars are the standard deviation for duplicate measurements.

Example 3—Selection of Low Copy-Number Target Nucleic Acid Molecules

The method of the present invention was used to detect a low copy number of genomic DNA targets in order to determine the sensitivity of the method of the present invention. 60 or 600 genomic targets were added to the test reactions, and both KRAS and SF3B1 genomic fragments were detected according to the method outlined in Example 4.

Both target regions of interest were detectable even at the 60 genomes level, indicating that the present method is highly sensitive and can detect a low copy-number of target nucleic acid molecules. Overall no significant differences were observed between the efficiency of detection for the probes with, and without the poly-T intervening sequences. The results of the low copy-number detection of the target nucleic acid fragments is shown in FIG. 10. A detection efficiency of 2.5% of 600 genomes was estimated for the SF3B1_T0 probe. Error bars are the standard deviation for duplicate measurements.

Example 4—Effect of a Barcode Sequence on Amplification Efficiency

Nucleic acid probes with and without an barcode sequence between the second and third target binding sites (i.e. a barcode sequence) were used to determine the effect that the barcode sequence had on amplification efficiency. The KRAS genomic fragment was detected according the method outlined in Example 4 using the KRAS_T1, KRAS_InT, and KRAS_A2 probes shown in Table 1. The KRAS_InT and KRAS_A2 probes comprise a barcode sequence between the second and third binding sites in the probe. As the KRAS_T1 probe had already been shown to be as effective as the KRAS_T0 probe for selecting the KRAS target fragment, it was used as the positive control probe for this experiment.

No significant loss of signal was observed when using probes containing a barcode sequence (i.e. KRAS_InT and KRAS_A2) in comparison to the KRAS_T1 probe. No significant difference in signals was observed when probes with a polyT (kRAS_InT) insertion were used in comparison to probes with a polyA (kRAS_pA2) insertion. The results of the amplification of the KRAS target region of interest are shown in FIG. 11. A detection efficiency of ~2% was estimated for KRAS_InT probes. Error bars are the standard deviation for duplicate measurements.

Example 5—Mutation Detection by Nucleic Acid Probes and superRCA Readout

KRAS G12A Genomic DNA reference standards (wild-type and mutant (50%)) were purchased from Horizon Diagnostics and the region of interests (ROI) were enriched by PCR using primers reaching out fragments for complete binding of CutLig probes. Approximately 1.5e9 enriched fragments were mixed with 100 fold excess of probes and processed according to the protocol described in Example 4. One µl of SuperRCA padlock mix was added to 15 µl RCA mix reaching final concentrations of 0.05 mM ATP (Thermo Scientific), 100 nM of each padlock and 0.04 Weiss U/µl T4 DNA ligase (Thermo Scientific). The reaction was incubated at 37° C. for 30 min, followed by addition of 1.2 µl $2^{nd}$ RCA mix reaching final concentrations of 1 mM dNTP, 500 nM $2^{nd}$ RCA primer, 100 nM of each Cy3 or Cy5 labelled detection oligonucleotides and 0.1 U/µl phi29 DNA polymerase. The RCA reaction was carried out at 37° C. for 120 min. Four µl of RCA products were deposited on a poly-L-lysine coated glass slide (Sigma-Aldrich), followed by image acquisition using 20× objective of an Axioplan II epifluorescence microscope (Zeiss) with excitation and emission filters for Cy3 and Cy5 and exposure time of 1000 ms.

SuperRCA products were generated for both the wildtype and mutant DNA sequences. Mutant amplification product was detected in the red channel, and wild-type amplification product was detected in the green channel. The mixture of the mutant and wild-type DNA sequences were detected in the red and green channels in equal number, whereas the wild-type sequences were only detected in the green channel. FIG. 12 shows the results of the mutant detection in the KRAS gene.

Example 6—Demonstration of Reduced Unwanted-Target-Digestion Using Nucleic Acid Probes A direct comparison of the effect of AluI on reducing the signal obtained when selecting a target nucleic acid sequence was made between the known "selector" method of selecting a target region of interest as described in U.S. Pat. No. 7,883,849, and the method disclosed in the present invention.

For the method of the invention (CutLig approach), approximately 3e6 human male genomes (Promega) were incubated with 25 nM probes in 20 µl 0.5×PBS and heated at 95° C. for 20 min, followed by immediate chill on ice. 27 µl cutting mix containing 1× CutSmart buffer, 0.05 U/µl HaeIII, 0.05 U/µl MboI was added to 3 µl target and probe mix, followed by incubation at 37° C. for 30 min and 85° C. for 20 min. For Selector approach, approximately 3e6 human male genomes were incubated in 30 µl 1× CutSmart buffer, 0.05 U/µl HaeIII, 0.05 U/µl MboI at 37° C. for 30 min and 85° C. for 20 min. 2 µl of the digested products were incubated with 18 µl 2.5 nM probes in 0.5×PBS at 95° C. for 20 min, followed by immediate chill on ice.

AluI was added to the cutting mix in both approaches for digestion of double stranded target region of interest. 3 µl of the products from each approach were then incubated in 30 µl of 1× ampligase buffer, 0.02 U/µl ampligase at 55° C. for 15 min. 6 µl of the ligation products were RCA amplified in 30 µl of 1×EINAR buffer (50 mM KAc, 20 mM Tris-HAc pH 7.6, 3 mM MgAC$_2$), 0.2 µg/µl BSA, 0.25 mM d(A, T, G, C)TP and 0.02 U/µl phi29 DNA polymerase at 37° C. for 60 min and 65° C. for 15 min. 10 µl RCA products were added to 15 µl PCR mix reaching final concentrations of 1×EINAR buffer, 100 nM PCR primers, 0.5×SYBR, 0.06 U/µl platinum Taq DNA polymerase 0.2 mM d(A, U, G, C)TP, 0.002 U/µl UNG. Real time PCR was carried out in Stratagene MX3005 PCR machine (Agilent Technologies) using a thermal profile with an initiation at 95° C. for 2 min followed by 45 cycles of 95° C. for 15 sec and 60° C. for 1 min.

AluI cuts double-stranded DNA at the sequence AGCT, which is located at two separate locations within the target region of interest in the KRAS gene. FIG. 13 shows the effect of AluI on the level of amplification product for both the selector method and the method of the present invention. The extent of cleavage of the DNA product of the present invention is substantially lower than that seen for the selector method, as the target region of interest is single-stranded during the restriction digestion step of the method of the present invention (as the nucleic acid probes of the present invention do not comprise a sequence capable of binding to the target region of interest). This demonstrates that a particular restriction enzyme may be used in the methods of the present invention, even when the target region of interest contains the recognition sequence for that particular restriction enzyme, without significantly degrading the target region of interest or affecting the sensitivity of the selection method.

In the methods of the prior art it was previously necessary to avoid using restriction enzymes which had recognition sequences within the target region of interest, as the double-stranded products produced would be degraded. In contrast to this, in the method of the present invention such a restriction enzyme or enzymes may be used, as the target region of interest is not degraded. This is of particular interest in the multiplexing aspect of the present invention, where it may be desirable to use many different restriction enzymes when selecting a plurality of target regions of interest, as it is no longer necessary to avoid using a particular restriction enzyme due to the presence of a particular sequence within one or more of the plurality of target regions of interest. Thus a larger number of restriction enzymes may be used in the multiplexed selection of a plurality of target nucleic acids than was previously possible, and thus the present invention enables a higher degree of multiplexing to take place.

The invention claimed is:

1. A method of selecting a target region of interest (ROI) in a target nucleic acid molecule, said method comprising:
   (a) providing a probe comprising in the following order four target-binding sites capable of hybridising to complementary binding sites in the target molecule, which complementary binding sites flank the target ROI, as follows:
   (i) a first target-binding site, complementary to a first outer flanking sequence flanking a first side of the ROI in the target molecule;
   (ii) a second target-binding site, complementary to a second inner flanking sequence flanking the other side of the ROI on the target molecule;
   (iii) a third target-binding site, complementary to a first inner flanking sequence flanking the first side of the ROI in the target molecule;
   (iv) a fourth target-binding site, complementary to a second outer flanking sequence flanking the other side of the ROI in the target molecule;
   such that only one of the second and third binding sites are able to hybridise to their respective complementary binding site in the target molecule when said first and fourth binding sites have hybridised;
   wherein the first and fourth binding sites comprise a sequence capable of creating a cleavage site when hybridised to the target molecule;
   (b) contacting the probe with the target molecule and allowing the first, fourth and one of the second and third target binding sites to hybridise to their respective complementary binding sites in the target molecule, wherein the target molecule is at least partially single stranded including in the region comprising the four complementary binding sites, such that when said probe has bound a partially double-stranded construct is created comprising a loop in the probe strand comprising the second or third target binding site which did not hybridise to the target molecule and a loop in the target molecule strand comprising the ROI and the complementary binding site which is complementary to the second or third target binding region of the probe which did not hybridise;
   (c) cleaving the probe/target molecule construct at the cleavage sites created by hybridisation of the first and fourth target-binding sites thereby to release a target fragment comprising the ROI flanked by the first and second inner flanking sequences which are complementary to the third and second target binding regions of the probe, one of which is hybridised to its complementary binding site in the cleaved probe;
   (d) allowing the second or third target-binding site of the probe which did not hybridise in step (b) to hybridise to its complementary binding site in the target fragment, thereby to bring the ends of the target fragment into juxtaposition for ligation, directly or indirectly, using the cleaved probe as ligation template;
   (e) ligating the ends of the target fragment directly or indirectly to circularise the target fragment; and
   (f) amplifying or separating the circularised target fragment, thereby to select the ROI.

2. The method of claim 1, wherein a plurality of probes are used to select a plurality of target regions of interest, wherein each probe is designed to select a different target region of interest.

3. The method of claim 1, wherein a single probe is used to select a plurality of different target regions of interest within corresponding target molecules from a plurality of samples.

4. The method of claim 1, wherein the first and fourth target binding sites are situated at the ends of the probe.

5. The method of claim 1, wherein the four binding sites are immediately adjacent to one another.

6. The method of claim 1, wherein the probe further comprises one or more intervening sequences between any two of the binding sites.

7. The method of claim 6, wherein the intervening sequence is a capture sequence.

8. The method of claim 7, wherein the capture sequence hybridises to a cognate complementary binding site provided on a solid surface.

9. The method of claim 7, wherein the capture sequence or a complementary oligonucleotide hybridised thereto is attached to an affinity binding moiety.

10. The method of claim 7, wherein a capture sequence is provided between the first and second and/or between the third and fourth binding sites.

11. The method of claim 6, wherein the intervening sequence is or comprises a tag sequence or a complement thereof, wherein the tag sequence is selected from a detection sequence or an identification sequence element or a binding site for a primer or detection probe.

12. The method of claim 11, wherein the tag sequence is an identification element for the target ROI or a sample identification sequence.

13. The method of claim 1, wherein the second and third binding sites are immediately adjacent to one another and the ends of the target fragment are ligated directly to one another.

14. The method of claim 6, wherein an intervening sequence lies between the second and third binding sites, thereby creating a gap between the respective ends of the target fragment when they are both hybridised to the second and third binding sites in step (d), and wherein the gap is filled prior to ligation by one or more gap oligonucleotides which hybridise in the gap between the ends of the target fragment, or by gap-fill extension of the 3' end of the hybridised target fragment using a polymerase, such that the target fragment and any gap oligonucleotides if present may be ligated into a circular molecule comprising the target fragment.

15. The method of claim 14, wherein the gap oligonucleotide(s) comprise(s) a tag sequence complementary to a tag sequence complement in the intervening sequence.

16. The method of claim 14, wherein the gap oligonucleotide comprises a region which is not complementary to the intervening sequence, and wherein the region of non-complementarity comprises a tag sequence.

17. The method of claim 14, wherein the gap oligonucleotide comprises a detection sequence or an identification sequence element, or a binding site for an amplification primer or a detection probe.

18. The method of claim 17, wherein the amplification primer is a universal amplification primer.

19. The method of claim 14, which is performed in multiplex using a plurality of different probes and wherein the gap oligonucleotide for each probe comprises the same tag sequence.

20. The method of claim 14, wherein the gap oligonucleotide is pre-hybridised to the probe prior to contacting the probe with the target nucleic acid molecule.

21. The method of claim 14, wherein the gap oligonucleotide is separately provided at the same time or after contacting the probe with the target molecule.

22. The method of claim 6, wherein the probe comprises a hairpin structure containing one or more binding sites, such that they are not available for hybridisation to the target molecule until the probe is activated by unfolding the hairpin structure, and wherein the method comprises a further step of activating the probe by unfolding the hairpin structure by disruption of the duplex of the hairpin or by cleavage in or near the loop prior to or after contacting the probe with the target molecule.

23. The method of claim 22, wherein the stem of the hairpin is formed between an intervening sequence between the second and third binding sites of the probe, and an additional sequence provided at the end of the first binding site, and wherein cleavage of the loop at or near to the junction between the first target binding site and the additional sequence in the stem duplex releases the first and second binding sites.

24. The method of claim 23, wherein cleavage is enzymatic cleavage.

25. The method of claim 1, wherein the cleavage sites created in step (b) are restriction sites.

26. The method of claim 1 wherein amplification of the circularised target fragment is by PCR or Rolling Circle Amplification (RCA).

27. The method of claim 26, wherein amplification is by RCA, and wherein amplification further comprises a second round of RCA.

28. The method of claim 1 further comprising a step of detecting and/or analysing the circularised target fragment or an amplicon thereof.

29. The method of claim 28, wherein the amplified product is detected by hybridising a detection probe labelled with a directly or indirectly detectable label to the amplification product.

30. The method of claim 29, wherein the detection label is a fluorescent label.

31. The method of claim 28, wherein the target fragment or amplicon thereof is detected or analysed by sequencing.

32. A probe for use in the method of claim 1, wherein said probe is DNA and comprises, in the following order, four target-binding sites capable of hybridising to complementary binding sites in the target molecule, which complementary binding sites flank the target ROI, as follows:
  (i) a first target-binding site, complementary to a first outer flanking sequence flanking a first side of the ROI in the target molecule;
  (ii) a second target-binding site, complementary to a second inner flanking sequence flanking the other side of the ROI on the target molecule;
  (iii) a third target-binding site, complementary to a first inner flanking sequence flanking the first side of the ROI in the target molecule;
  (iv) a fourth target-binding site, complementary to a second outer flanking sequence flanking the other side of the ROI in the target molecule;
  such that only one of the second and third binding sites are able to hybridise to their respective complementary binding site in the target molecule when said first and fourth binding sites have hybridised; and
  wherein the first and fourth binding sites comprise a sequence capable of creating a cleavage site when hybridised to the target molecule.

33. A kit for selecting a target region of interest in a target nucleic acid molecule, said kit comprising:

a) a probe as defined in claim 32 and optionally one or more components selected from:
b) means for cleaving the cleavage sites created by hybridisation of the probe;
c) means for unfolding a hairpin structure in the probe;
d) a ligase enzyme;
e) one or more gap oligonucleotides;
f) means for amplification of the circularised target fragment; and
g) means for detecting the circularised target fragment or an amplicon thereof.

34. The method of claim 19, wherein the gap oligonucleotide for each probe comprises the same primer binding site.

35. The probe of claim 32, wherein the first and fourth binding sites comprise a sequence capable of creating a cleavage site comprising a restriction site when hybridised to the target molecule.

36. The probe of claim 32, wherein the probe is linear.

37. A sample comprising a target nucleic acid molecule and a probe,
wherein the target nucleic acid molecule comprises a target region of interest (ROI), a first outer flanking sequence flanking a first side of the ROI, a second inner flanking sequence flanking the other side of the ROI on the target molecule, a first inner flanking sequence flanking the first side of the ROI in the target molecule, and a second outer flanking sequence flanking the other side of the ROI in the target molecule; and
wherein said probe is DNA and comprises, in the following order, four target-binding sites capable of hybridising to complementary binding sites in the target molecule which flank the ROI, as follows:
(i) a first target-binding site, complementary to the first outer flanking sequence in the target molecule;
(ii) a second target-binding site, complementary to the second inner flanking sequence;
(iii) a third target-binding site, complementary to the first inner flanking sequence;
(iv) a fourth target-binding site, complementary to the second outer flanking sequence;
such that only one of the second and third binding sites are able to hybridise to their respective complementary binding site in the target molecule when said first and fourth binding sites have hybridised; and
wherein the first and fourth binding sites comprise a sequence capable of creating a cleavage site when hybridised to the target molecule.

* * * * *

SEQUENCE LISTING

<160> NUMBER OF SEQ ID NOS: 19

<210> SEQ ID NO 1
<211> LENGTH: 170
<212> TYPE: DNA
<213> ORGANISM: Homo sapiens

<400> SEQUENCE: 1
gtcacatttt cattattttt attataaggc ctgctgaaaa tgactgaata taaacttgtg      60
gtagttggag ctggtggcgt aggcaagagt gccttgacga tacagctaat tcagaatcat     120
tttgtggacg aatatgatcc aacaatagag gtaaatcttg ttttaatatg                170

<210> SEQ ID NO 2
<211> LENGTH: 109
<212> TYPE: DNA
<213> ORGANISM: Artificial Sequence
<220> FEATURE:
<223> OTHER INFORMATION: Synthesized

<400> SEQUENCE: 2
catattaaaa caagatttac ctctattgtt ggatcataca gtcattttca gcaggatatt      60
cgtccacaaa atgaagcagg ccttataata aaaataatga aaatgtgac                 109

<210> SEQ ID NO 3
<211> LENGTH: 142
<212> TYPE: DNA
<213> ORGANISM: Artificial Sequence
<220> FEATURE:
<223> OTHER INFORMATION: Synthesized

<400> SEQUENCE: 3
catattaaaa caagatttac ctctattgtt ggatcatatt ttttttttt tttttcagtc       60 attttcagca ggatattcgt ccacaaaatg atttttttt tttttttagc aggccttata     120
ataaaaataa tgaaaatgtg ac                                              142

<210> SEQ ID NO 4
<211> LENGTH: 157
<212> TYPE: DNA
<213> ORGANISM: Artificial Sequence
<220> FEATURE:
<223> OTHER INFORMATION: Synthesized

<400> SEQUENCE: 4

```
ctattaaaac aagatttacc tctattgttg gatcatatga atttcagcag ggataccgga    60
ccaggtttcg ccgattcgag aacgcagtgt catattcgtc cacaaaatga tgaaagcagg   120
ccttataata aaaataatga aaatgtgacg acactgc                            157
```

<210> SEQ ID NO 5
<211> LENGTH: 186
<212> TYPE: DNA
<213> ORGANISM: Artificial Sequence
<220> FEATURE:
<223> OTHER INFORMATION: Synthesized

<400> SEQUENCE: 5

```
ctattaaaac aagatttacc tctattgttg gatcatataa aaaaaaaaa aaaaaaaaa     60 aaatcagtca ttttcagcag ggataccgga ccaggtttcg ccgattcgag aacgcagtgt   120
catattcgtc cacaaaatga tgaaagcagg ccttataata aaaataatga aaatgtgacg   180
acactg                                                              186
```

<210> SEQ ID NO 6
<211> LENGTH: 40
<212> TYPE: DNA
<213> ORGANISM: Artificial Sequence
<220> FEATURE:
<223> OTHER INFORMATION: Synthesized

<400> SEQUENCE: 6

```
gacactgcgt tctcgaatcg gcgaaacctg gtccggtatc                          40
```

<210> SEQ ID NO 7
<211> LENGTH: 90
<212> TYPE: DNA
<213> ORGANISM: Artificial Sequence
<220> FEATURE:
<223> OTHER INFORMATION: Synthesized

<400> SEQUENCE: 7

```
gataccctcc cataaaggct ttaacacacc aaggcagcaa tggacacaga atcaaaagat    60
tcgcaatggc caaagcactg atggtccgaa                                     90
```

<210> SEQ ID NO 8
<211> LENGTH: 122
<212> TYPE: DNA
<213> ORGANISM: Artificial Sequence
<220> FEATURE:
<223> OTHER INFORMATION: Synthesized

<400> SEQUENCE: 8

```
gataccctcc cataaaggct ttaacacatt tttttttttt ttttccaagg cagcaatgga    60
cacagaatca aaagattcgt tttttttttt ttttcaatg gccaaagcac tgatggtccg   120
aa                                                                  122
```

<210> SEQ ID NO 9
<211> LENGTH: 22
<212> TYPE: DNA
<213> ORGANISM: Artificial Sequence
<220> FEATURE:
<223> OTHER INFORMATION: Synthesized

<400> SEQUENCE: 9

```
cgtgccttga cgatacagct aa                                             22
```

```
<210> SEQ ID NO 10
<211> LENGTH: 19
<212> TYPE: DNA
<213> ORGANISM: Artificial Sequence
<220> FEATURE:
<223> OTHER INFORMATION: Synthesized

<400> SEQUENCE: 10
caaggcactc ttgcctacg                                                  19

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11
gattctgtgt ccattgctgc                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthesized

<400> SEQUENCE: 12
gagttgctgc ttcagccaag                                                 20

<210> SEQ ID NO 13
<211> LENGTH: 146
<212> TYPE: DNA
<213> ORGANISM: Homo sapiens

<400> SEQUENCE: 13
gtcttgtgga tgagcagcag aaagttcgga ccatcagtgc tttggccatt gctgccttgg     60
ctgaagcagc aactccttat ggtatcgaat cttttgattc tgtgttaaag cctttatgga    120
agggtatccg ccaacacaga ggaaag                                         146

<210> SEQ ID NO 14
<211> LENGTH: 31
<212> TYPE: DNA
<213> ORGANISM: Artificial Sequence
<220> FEATURE:
<223> OTHER INFORMATION: Synthesized

<400> SEQUENCE: 14
catattaaaa caagatttac ctctattgtt g                                    31

<210> SEQ ID NO 15
<211> LENGTH: 49
<212> TYPE: DNA
<213> ORGANISM: Artificial Sequence
<220> FEATURE:
<223> OTHER INFORMATION: Synthesized

<400> SEQUENCE: 15
gatcatacag tcattttcag caggatattc gtccacaaaa tgaagcagg                 49

<210> SEQ ID NO 16
<211> LENGTH: 29
<212> TYPE: DNA
<213> ORGANISM: Artificial Sequence
<220> FEATURE:
```

```
<223> OTHER INFORMATION: Synthesized

<400> SEQUENCE: 16
ccttataata aaaataatga aaatgtgac                                        29

<210> SEQ ID NO 17
<211> LENGTH: 29
<212> TYPE: DNA
<213> ORGANISM: Homo sapiens

<400> SEQUENCE: 17
gtcacatttt cattattttt attataagg                                        29

<210> SEQ ID NO 18
<211> LENGTH: 106
<212> TYPE: DNA
<213> ORGANISM: Homo sapiens

<400> SEQUENCE: 18
cctgctgaaa atgactgaat ataaacttgt ggtagttgga gctggtggcg taggcaagag       60
tgccttgacg atacagctaa ttcagaatca ttttgtggac gaatat                    106

<210> SEQ ID NO 19
<211> LENGTH: 35
<212> TYPE: DNA
<213> ORGANISM: Homo sapiens

<400> SEQUENCE: 19
gatccaacaa tagaggtaaa tcttgtttta atatg                                 35
```